United States Patent [19]

Fujino et al.

[11] Patent Number: 5,159,061

[45] Date of Patent: Oct. 27, 1992

[54] ATRIAL NATRIURETIC PEPTIDE DERIVATIVE

[75] Inventors: Masahiko Fujino, Hyogo; Mitsuhiro Wakimasu, Osaka; Kohei Nishikawa, Kyoto, all of Japan

[73] Assignee: Takeda Chemical Industries, Ltd., Osaka, Japan

[21] Appl. No.: 101,199

[22] Filed: Sep. 25, 1987

[30] Foreign Application Priority Data

Sep. 29, 1986 [JP] Japan .................. 61-231429

[51] Int. Cl.$^5$ ............................................... C07K 7/10
[52] U.S. Cl. .................................................. 530/326
[58] Field of Search ........................ 530/326, 325, 324

[56] References Cited

U.S. PATENT DOCUMENTS

| | | |
|---|---|---|
| 4,508,712 | 4/1985 | Needleman . |
| 4,607,023 | 8/1986 | Thibault et al. . |
| 4,670,540 | 6/1987 | Sakakibara ..................... 530/324 |
| 4,757,048 | 7/1988 | Lewicki et al. ..................... 514/13 |

FOREIGN PATENT DOCUMENTS

| | | |
|---|---|---|
| 0164273 | 6/1985 | European Pat. Off. . |
| 0173557 | 8/1985 | European Pat. Off. . |
| 0182984 | 8/1985 | European Pat. Off. . |
| 0223143 | 3/1986 | European Pat. Off. ............ 530/326 |
| 0231752 | 1/1987 | European Pat. Off. . |
| 0246795 | 11/1987 | European Pat. Off. . |
| 286400 | 7/1986 | Japan . |
| 233698 | 9/1986 | Japan . |
| WO85/04870 | 11/1985 | PCT Int'l Appl. ..................... 530/324 |

OTHER PUBLICATIONS

Flynn, T. G.; Davies, P. L., Review Article, Biochem. J., 232: 313-321, 1985.

Chino, et al., Peptide Chemistry 1984: N. Izumiya (Ed.), Protein Res. Found., Osaka (1985), pp. 229-235.

Kanagawa et al. Purification and Complete Amino Acid Sequence of a-Human Atrial Natriuretic Polypeptide (a-hANP) "Biochemical and Biophysical Research Communications" vol. 118, No. 1, 1984, Jan. 13, 1984; pp. 131-139.

Chino et al. Synetheses of a-Human Atrial Natriuretic Polypeptide (a-hANP) and Its Peptides "Peptide Chemistry 1984: N. Izumiya (Ed.) Protein Research Foundation Osaka (1985)" pp. 240-247.

Minamitake et al. Syntheses and Biological Activities of a-Human Atrial Natriuretic Polypeptide and Its Analogs "Peptide Chemistry 1984: N. Izumiya (Ed.) Protein Research Foundation, Osaka (1985)" pp. 229-235.

C. M. Deber et al. (Chino) "Structure-Activity Study of -Human Atrial Natriuretic Polypeptide (-haNP)" Proceedings of the Amer. Peptide Symposium, Proc. 9, 1985, pp. 945-948.

*Primary Examiner*—Merrell C. Cashion, Jr.
*Assistant Examiner*—Susan M. Perkins
*Attorney, Agent, or Firm*—Wegner, Cantor, Mueller & Player

[57] ABSTRACT

A peptide derivative of the formula

A-

```
  ┌─────────────────────────────────────────────────┐
  CysPhe-B-Arg-C-Asp-Arg-Ile-Gly-Ala-Gln-Ser-Gly-Leu-Gly-Cys-
                                                  Asn-Ser-Phe-E-Tyr-OH
``` wherein A is hydrogen or a hydrocarbon acyl having 2 to 18 carbon atoms which is substituted by an amino group at the α-position; B is F-Gly wherein F is a neutral α-amino acid residue, or NH-(CH$_2$)nCO wherein n is an integer of 1 to 4; C is a neutral α-amino acid residue; and E is L-Arg or D-Arg; when A, B and C are hydrogen, Gly-Gly, and Met or Ile, respectively, E is D-Arg, or its pharmacologically acceptable salt has strong hypotensive and natriuretic activity; therefore it is useful as a therapeutic drug for hypertension, a diuretic, and a therapeutic drug for cardiac and cerebral circulatory diseases.

4 Claims, No Drawings

ATRIAL NATRIURETIC PEPTIDE DERIVATIVE

The present invention relates to an atrial natriuretic peptide derivative which is useful as a therapeutic drug for hypertension, a diuretic, a therapeutic drug for cardiac and cerebral circulatory diseases, a muscle relaxant.

Recently, 3 peptides having strong natriuretic activity have been isolated from the human atrium, and their structures have been clarified. Of these peptides, that with the lowest molecular weight, consisting of 28 amino acid fragments, was named α-human atrial natriuretic polypeptide (hereinafter referred to as a α-hANP) [Biochemical Biophysical Research Communications, 118, 131-139(1984)].

The structural formula of a α-hANP is shown below.

```
      1           5              10
H—Ser—Leu—Arg—Arg—Ser—Ser—Cys—Phe—Gly—Gly—Arg—Met—Asp—

15          20              25
Arg—Ile—Gly—Ala—Gln—Ser—Gly—Leu—Gly—Cys—Asn—Ser—Phe—Arg—
28
Tyr—OH
```

As a result of studies on the structure activity relationship of α-hANP, it was later found that α-hANP[7-28], which results from the shortening the N-terminus of α-hANP, has natriuretic activity equivalent to that of α-hANP. No short-chain peptide compound other than α-hANP[7-28] has been reported as having activity equivalent to, or stronger than that of α-hANP [PEPTIDE CHEMISTRY 1984, edited by N. IZUMIYA, pp. 229-234, 241-244(1984)].

Non-peptide hypotensive diuretics have conventionally been used s therapeutic drugs for hypertension, but they have been known to cause side effects in the case of heart disease; safer drugs are therefore desirable. With respect to this, α-hANP is considered to have the potential for being a very safe drug. However, there are still many problems to be solved, such as enzymatic decomposition and short action time, because it is an endogenous peptide itself.

Taking note of the fact that α-hANP[7-28] exhibits hypotensive and natriuretic actions equivalent to those of α-hANP, while all other short-chain peptides show extremely decreased action, the present inventors worked to synthesize a new α-hANP derivative with excellent enzyme tolerance, enduring action etc. as mentioned above. As a result, the present inventors found that the new compound in the present invention has strong hypotensive and natriuretic activity, and thus completed the present invention.

The present invention relates to
(1) a peptide derivative of the formula

```
         ┌─────────────────────────────────────────────────
A—Cys—Phe—B—Arg—C—Asp—Arg—Ile—Gly—Ala—Gln—Ser—Gly—Leu—
─────────────┐
Gly—Cys—Asn—Ser—Phe—E—Tyr—OH
```
[I]

wherein A is hydrogen or a hydrocarbon acyl having 2 to 18 carbon atoms which is substituted by an amino group at the α-position; B is F-Gly wherein F is a neutral α-amino acid residue, or NH—(CH$_2$)nCO wherein n is an integer of 1 to 4; C is a neutral α-amino acid residue, and E is L-Arg or D-Arg; when A, B and C are hydrogen, Gly-Gly and Met or Ile, respectively, E is D-Arg, or its pharmacologically acceptable salt; and (2) a method for producing a peptide derivative of the formula [I] or its pharmacologically acceptable salt, which comprises subjecting a peptide derivative of the formula A-Cys-Phe-B-Arg-C-Asp-Arg-Ile-Gly-Ala-Gln-Ser-Gly-Leu-Gly-Cys-Asn-Ser-Phe-E-Tyr-OH [II]

wherein A, B, C and E have the same meaning as defined above, or its pharmacologically acceptable salt, to oxidation.

In the present specification, amino acids and peptides are also represented by abbreviations which are used commonly in related fields or specified by the IUPAC-IUB Commission on Biochemical Nomenclature, as shown below. It should be noted that the L-form is meant unless optical configuration is specified.

Ala: Alanine
Asp: Aspartic acid
Asn: Asparagine
Cys: Cysteine
Glu: Glutamic acid
Gln: Glutamine
Phe: Phenylalanine
Gly: Glycine
Ile: Isoleucine
Leu: Leucine
Met: Methionine
Ser: Serine
Tyr: Tyrosine
Trp: Tryptophane
Arg: Arginine
βAla, β-Ala: β-alanine
Gaba: γ-aminobutyric acid
Ava: 5-aminovaleric acid
Aca: 8-aminocaprylic acid
Chg: 2-cyclohexylglycine
Aib: α-aminoisobutyric acid
Achc: 1-amino-1-cyclohexanecarboxylic acid
Gua: Guanidinoacetic acid The protective groups and reagents mentioned frequently in the text are represented by the following abbreviations:

Z: Carbobenzoxy
Box: t-tutoxycarbonyl

Bzl: Benzyl
MBzl: p-methoxybenzyl
Ac: Acetyl
Pme: Pentamethylbenzenesulfonyl
Mtr: 4-methoxy-2,3,6-trimethylbenzenesulfonyl
OBzl: Benzyl ester
ObBu$^t$: t-butyl ester
DCC: N,N'-dicyclohexylcarbodiimide
DCU: N,N'-dicyclohexylurea
HONB: N-hydroxy-5-norbornane-2,3-dicarboxyimide
-ONB: HONB ester
HOBt: 1-hydroxybenzotriazole
Box-ON: 2-t-butoxycarbonyloxyimino-2-phenylacetonitrile
TEA: Triethylamine
CHA: Cyclohexylamine
DCHA: Dicyclohexylamine
p-Tos-OH: Paratoluenesulfonic acid
AcOH: Acetic acid
TFA: Trifluoroacetic acid
HF: Anhydrous hydrogen fluoride
HCl: Hydrochloric acid
AcOEt: Ethyl acetate
DMF: N,N-dimethylformamide
MeOH: Methanol In the present invention, the hydrocarbon acyls having 2 to 18 carbon atoms in the hydrocarbon acyls having 2 to 18 carbon atoms which are substituted by an amino group at the α-position, represented by A, include aliphatic, aromatic and ali-aromatic hydrocarbon acyls. The hydrocarbon acyls preferably have 3 to 5 carbon atoms.

For the aliphatic hydrocarbon acyl, any aliphatic hydrocarbon acyls can be used, whether saturated or unsaturated, and whether straightchained, branched, or cyclic. As examples of such aliphatic hydrocarbon acyls, mention may be made of acetyl, propionyl, butyryl, isobutyryl, valeryl, isovaleryl, pivaloyl, caproyl, caprylyl, capryl, lauroyl, myristoyl, palmitoyl, stearoyl, cyclobutaecarbonyl, cyclopentanecarbonyl, cyclohexanecarbonyly, oleoyl, and linoleyl etc.

As examples of the aromatic or ali-aromatic hydrocarbon acyls, mention may be made of benzoyl, phenylacetyl and phenylpropionyl etc.

As examples of hydrocarbon acyls substituted by (an) amino group(s) at the α-position, mention may be made of amino acid residues such as Ala, Val, Leu, Ile, nor-Leu, Phe, Lys, Aib, 1-amino-1-cyclobutanecarboxylic acid, 1-amino-1-cyclopentanecarboxylic acid, 1-amino-1-cyclohexanecarboxylic acid, 2-phenyl-Gly, 2-aminocaproic acid and 2-aminocapric acid etc.; when an optical isomer is present, it does not matter whether the amino acid is an L-form or a D-form.

Neutral α-amino acids for the neutral α-amino acid residue are represented by F in F-Gly as a substituent represented by B include neutral α-amino acids having 2 to 10 carbon atoms. As examples of such neutral α-amino acids, mention may be made of Gly, Ala, Val, Leu, Ile, nor-Leu, Met, Met sulfoxide, Met sulfone, Ser, Thr, Asn, Gln, Phe, Tyr, Trp, His Pro, Cys, Aib, 1-amino-1-cyclobutanecarboxylic acid, 1-amino-1-cyclopentanecarboxylic acid, 1-amino-1-cyclohexanecarboxylic acid, 2-cyclohexylglycine, 2-phenylglycine, 2-aminocaproic acid and 2-aminocapric acid; Gly, Ala, Val, Leu, Ile, nor-Leu, Met, Met sulfoxide, Phe, Trp, Ser and Thr are preferable.

When an optical isomer is present, it does not matter whether the amino acid is an L-form or a D-form.

As examples of groups represented by —NH—(CH$_2$)$_n$—CO wherein n is an integer of 1 to 4 for the substituent represented by B, mention may be made of Gly, β-Ala, Gaba and Ava etc.

Neutral α-amino acids for the neutral α-amino acid residue represented by C include those mentioned above for B; Gly, Ala, Val, Leu, Ile, nor-Leu, Met, Phe, 2-cyclohexylglycine, Trp etc. are preferable. When an optical isomer is present, it does not matter whether the amino acid is an L-form or a D-form.

The method for producing the peptide derivative (I) of the present invention is described below.

The peptide derivative (I) of the present invention can be produced by conventional methods of peptide synthesis. Any of the solid-phase and liquid-phase synthesis methods can be used, but the latter is more appropriate in many cases. Such methods of peptide synthesis may be carried out in accordance with any well-known method. Peptide synthesis methods which can be used include the methods described in PEPTIDE SYNTHESIS, M. Bodansky and M. A. Ondetti, Interscience, New York, 1966; THE PROTEINS, Vol. 2, F. M. Finn and K. Hofmann, edited by H. Nenrath and R. L. Hill, Academic Press Inc., New York, 1976; and "The Basis and Experiment of Peptide Synthesis", Nobuo Izumiya et al., Maruzen, 1985, such as the azide method, the chloride method, the acid anhydride method, the mixed acid anhydride method, the DCC method, the active ester method, the method using Woodward reagent-K, the carbodiimidazole method, the oxidation-reduction method and the DCC/NONB method etc.

The compound (I) of the present invention can be produced by condensing together two starting materials: one which has a reactive carboxyl group corresponding to one of the 2 fragments which part at an arbitrary position of peptide bond, and another which has a reactive amino group corresponding to the second fragment, by a conventional method of peptide synthesis, and oxidizing the resulting condensate, if the condensate has a protective group, after eliminating the protective group by a conventional method.

The method of protecting functional groups which are not meant to be involved in the starting material reaction, the protective groups themselves, and the method of activating functional groups involved in the reaction can also be suitably selected from conventional groups or methods.

As examples of protective groups for the amino group of the starting material, mention may be made of carbobenzoxy, t-butyloxycarbonyl, t-amyloxycarbonyl, isobornyloxycarbonyl, p-methoxybenzyloxycarbonyl, 2-chloro-benzyloxycarbonyl, adamantyloxycarbonyl, p-methoxybenzyloxycarbonyl, 2-chloro-benzyloxycarbonyl, adamantyloxycarbonyl, trifluoroacetyl, phthalyl, formyl, o-nitrophenylsulfenyl, diphenylphosphinothioyl and 9-fluorenylmethyloxycarbonyl etc. As examples of protective groups for the carboxyl group, mention may be made of alkyl ester (e.g. ester groups such as methyl, ethyl, propyl, butyl and t-butyl), benzyl ester, p-nitrobenzyl ester, p-methoxybenzyl ester, p-chlorobenzyl ester, benzhydryl ester, phenacyl ester, carbobenzoxyhydrazide, t-butyloxycarbonylhydrazide and tritylhydrazide etc.

As examples of protective groups for the thiol of cysteine, mention may be made of para-methoxybenzyl, 4-methylbenzyl, benzyl, t-butyl, adamantyl, trityl, acetamidomethyl, carbomethoxysulfenyl and 3-nitro-2-pyridinesulfenyl etc.

As examples of protective groups for the guanidino group of arginine, mention may be made of nitro, tosyl, p-methoxybenzenesulfonyl, mesitylenesulfonyl, pentamethyl benzenesulfonyl, 4-methoxy-2,3,6-trimethylbenzenesulfonyl, carbobenzoxy, isobornyloxycarbonyl and adamantyloxycarbonyl etc. The guanidino group may be protected in the form of a salt of acid (e.g. benzenesulfonic, toluenesulfonic, hydrochloric or sulfuric acid).

The hydroxyl group of serine may, for example, be protected by esterification or etherification. As examples of groups suitable for this esterification, mention may be made of lower alkanoyl groups such as acetyl group; aroyl groups such as benzoyl group; and groups derivable from carbonic acid such as benzyloxycarbonyl group and ethyloxycarbonyl group etc. Groups which are suitable for the etherification include benzyl group, tetrahydropyranyl group and t-butyl group etc. However, it is not always necessary to protect the hydroxyl group of serine.

As examples of protective groups for the phenolic hydroxyl group of tyrosine, mention may be made of benzyl, 2,6-dichlorobenzyl and 2-nitrobenzyl etc. but it is not always necessary to protect the phenolic hydroxyl group.

As examples of protective groups for the β-carboxyl of aspartic acid, mention may be made of benzyl ester, p-nitrobenzyl ester, p-chlorobenzyl ester and alkyl ester (e.g. t-butyl ester, cyclopentyl ester, cyclohexyl ester and cycloheptyl ester) etc. The methionine may be protected in the form of sulfoxide.

As examples of the activated carboxyl group of the starting material, mention may be made of the corresponding acid anhydrides, azide and active esters [esters with alcohol (e.g. pentachlorophenol, 2,4,5-trichlorophenol, 2,4-dinitrophenol, cyanomethyl alcohol, p-nitrophenol, N-hydroxy-5-norbornane-2,3-dicarboxyimide, N-hydroxysuccimide, N-hydroxyphthalimide and N-hydroxybenztriazole). As examples of the activated amino group of the starting material, mentioned may be made of the corresponding phosphamides.

The condensation can be carried out in the presence of a solvent. The solvent can be suitably selected from solvents which are known to be useful in the peptide condensing reaction. As examples of such solvents, mention may be made of anhydrous or hydrous dimethylformamide, dimethylsulfoxide, pyridine, chloroform, dioxane, dichloromethane, tetrahydrofuran, acetonitrile, ethyl acetate, N-methylpyrrolidone and suitable mixtures thereof.

Reaction temperature can be suitably selected from the range which can be used for the peptide bond-forming reaction, normally, in the range of about $-20°$ to $30°$ C. The precursor (protected peptide) of the compound of the present invention can also be easily produced by the solid-phase synthesis method.

The protected peptide thus obtained is then subjected to a deprotecting reaction. This reaction depends on the type of protective group used, but, in any case, it is favorable in industrial manufacture to eliminate all protective groups in a single process without affecting the peptide bond. Protective groups are therefore selected bearing in mind this aspect. In the case of cysteine-containing peptide, however, it is sometimes more favorable to eliminate the protective groups in 2 steps, i.e., to first eliminate the protective groups other than those for thiol, followed by the elimination of the protective groups for thiol, since purification is easy. As examples of protective groups for thiol used in this case, mention may be made of acetamidomethyl group and 3-nitro-2-pyridinesulfenyl group.

Possible means for eliminating protective groups include acid treatment using, for example, anhydrous hydrogen fluoride, methanesulfonic acid, trifluoromethanesulfonic acid, trifluoroacetic acid or a mixed solution thereof; mention may also be made of reduction in liquid ammonia by means of sodium. The above deprotecting reaction by acid treatment is normally carried out at a suitable temperature of $-20°$ to $40°$ C.; the addition of a cation scavenger such as anisole, phenol, thioanisole or dimethylsulfide is effective in the acid treatment. Protective groups for thiol that are stable to acid treatment such as acetamidomethyl and 3-nitro-2-pyridinesulfenyl can be eliminated with iodine or mercury acetate in the former case, and with mercaptoethanol or similar in the latter.

When the neutral α-amino acid residue represented by B or C is Cys, only the protective groups held by amino acids other than the said Cys are previously eliminated, followed by oxidation by the method described below, and then the protective groups for the said Cys are eliminated.

The thiol peptide thus obtained by eliminating the protective groups of the protected peptide is subjected to oxidation.

Possible methods of oxidation include methods that are carried out in a solvent such as water, or that use air, potassium ferricyanide, iodine, diiodoethane or the like.

It is normally desirable that the above oxidation be carried out by the high dilution method at the appropriate temperature of about $0°$ to $40°$ C. and at a pH of about 6 to 7.5.

The peptide derivative (I) thus produced is collected by means of a peptide separation such as extraction, partition, reprecipitation, recrystallization or column chromatography, after completion of the reaction.

The peptide derivative (I) of the present invention may also be obtained in the form of an acid-adduct of a salt, specifically a pharmacologically acceptable acid-adduct of a salt, by a known method. As examples of such salts, mention may be made of the salts of inorganic acids (e.g. hydrochloric acid, sulfuric acid and phosphoric acid) or organic acids (e.g. acetic acid, propionic acid, citric acid, tartaric acid, malic acid, oxalic acid and methanesulfonic acid) etc.

The pharmacological action of the peptide derivative of the present invention is described below.

Hypotensive action in spontaneously hypertensive rats (SHR)

Three male SHRs at the age of 20 weeks in each group were anesthetized with pentobarbital (50 mg/kg, intraperitoneal administration); SP-10 and SP-45 polyethylene tubes (manufactured by Natsume Seisakusho, Japan) were inserted respectively into the groin artery and vein, and through each of these a cannula was passed to the neck site via the back subcutaneous tissue, and one end of the cannula was fixed there. The rats were used in experiments the following day. As a α-hANP derivatives, [Aib$^6$]-α-hANP[6-28] obtained in Example 1 and [Aib$^6$,Ile$^{12}$]-α-hANP[6-28] obtained in Example 8, and as a control, α-hANP[7-28], in solution in physiological saline, were each intravenously administered in the ratio of 100 μg/250 μl/kg of body weight. Hypotensive activities are shown as a degree of the maximum decrease in blood pressure (difference from the preadministration value) that occurred after the administration of the subject compound.

| Hypotensive Activities in SHR | |
|---|---|
| | Degree of Decrease in Blood Pressure (ΔmmHg) |
| α-hANP[7-28] | −22 |
| [Aib⁶]-α-hANP[6-28] | −70 |
| [Aib⁶, Ile¹²]-α-hANP[6-28] | −90 |

The peptide derivative (I) of the present invention and its salts exhibit strong hypotensive action in spontaneously hypertensive rats (SHR), and, in addition, the action is stronger than that of any known α-hANP derivative.

In addition, the peptide derivative (I) of the present invention and its salts are generally low in toxicity.

The peptide derivative (I) of the present invention, or its salt, can therefore be used to treat hypertension, heart failure, nephritis, peripheral circulatory failure or similar conditions in mammals (e.g. mice, rats, rabbits, dogs, cats and humans).

The peptide derivative of the present invention can be administered in the form of a free base or acid-adduct of its salt. The dosage is normally an appropriate level in the range of 1 ng to 10 mg per kg of body weight, calculated as a free base, for both free bases and acid-adduct salts of the derivative (I). The derivative of the present invention is principally parenterally administered (e.g. by intravenous or subcutaneous injection, intraventricular, intraspinal, nasal or rectal administration); in some cases, however, it is orally administered.

Dosage forms which can be used include injection and suppository. The derivative of the present invention is stable as a substance, and therefore it may be stored in solution in physiological saline, but it may also be lyophilized in the presence of mannitol or sorbitol to form an ampule, and may be dissolved before use.

EXAMPLES

The present invention is hereinafter described in more detail with some examples. Sephadex LH-20 used to purify the final product is produced by Pharmacia Biotechnology, Sweden. The purities of the produced compounds were determined by thin layer chromatography using Kiesel Gel 60F-254 (Merck, West Germany). The developing solvents used are as follows:

Rf¹: Chloroform-methanol (19:1)
Rf²: Chloroform-methanol-acetic acid (9:1:0.5)
Rf³: Chloroform-methanol-water (7:3:0.5)
Rf⁴: Ethyl acetate-n-butanol-acetic acid-water (1:1:1:1)

EXAMPLE 1

Production of [Aib⁶]-α-hANP[6-28]

(I) Production of Boc-Arg(Pme)-Tyr(Bzl)-OBzl 5.6 g Boc-Tyr(Bzl)-OBzl was dissolved in 30 ml TFA, and concentrated, then 10 ml of 3N-HCl/dioxane was added. Ether was then added to precipitate a crystal, which was then collected by filtration and dried. The dry crystal was dissolved in 50 ml DMF and cooled with ice, then 1.9 ml TEA, 5.8 g Boc-Arg(Pme)-OH, 1.78 g HOBt and 2.72 g DCC were added, and this was followed by agitation for one night. The resulting DCU was filtered; this filtrate was concentrated; the resulting residue was dissolved in AcOEt; the resulting solution was washed with 4% aqueous NaHCO₃ and 10% aqueous citrate, and then with water, after which it was dried with Na₂SO₄. After filtering the dessicating agent, the filtrate was concentrated, and the resulting residue was precipitated with ether and collected by filtration.

Yield: 9.15 g (recovery: 92.0%).
m.p.: 114° to 116° C., Rf¹: 0.39.
$[\alpha]_D^{25}$: −5.2°(c=1.0, in DMF).
Elemental analysis (as $C_{45}H_{57}N_5O_8S$): Calculated: C, 65.27; H, 6.94; N, 8.46; S, 3.87. Found: C, 65.29; H, 67.05; N, 8.34; S, 3.86.

(II) Production of Boc-Phe-Arg(Pme)-Tyr(Bzl)-OBzl 9.0 g Boc-Arg(Pme)-Tyr(Bzl)-OBzl was treated with TFA in the same manner as in Example 1-(I); the amine component thus obtained was dissolved in 100 ml acetonitrile and cooled with ice, then 4.4 ml TEA was added. To this mixture Boc-Phe-ONB (prepared with 3.2 g Boc-Phe-OH, 2.4 g HONB and 2.7 g DCC) was added, and this was followed by agitation for one night. To this mixture 1 ml (CH₃)₂N(CH₂)₃NH₂ was added, followed by shaking for 30 minutes, then the mixture was concentrated. The resulting residue was dissolved in 300 ml AcOEt; the resulting solution was washed with 4% aqueous NaHCO₃ and 10% aqueous citrate, after which it was dried with Na₂SO₄. The dried matter was concentrated, then the resulting residue was precipitated with ether and collected by filtration.

Yield: 10.2 g (95.9%).
m.p.: 136° to 137° C., Rf¹: 0.39.
$[\alpha]_D^{25}$: −8.5°(c=0.9, in DMF).
Elemental analysis (as $C_{54}H_{66}N_6O_9S$): Calculated: C, 66.51; H, 6.82; N, 8.62; S, 3.29. Found: C, 66.56; H, 6.91; N, 8.61; S, 3.22.

(III) Production of Boc-Ser(Bzl)-Phe-Arg(Pme)-Tyr(Bzl)-OBzl 9.8 g Boc-Phe-Arg(Pme)-Tyr(Bzl)-OBzl was treated with TFA in the same manner as in Example 1-(I); the amine component thus obtained was dissolved in 100 ml DMF and cooled with ice, then 3 ml TEA was added. To this mixture Boc-Ser(Bzl)-ONB (prepared with 3.6 g Box-Ser(Bzl)-OH, 2.4 g HONB and 2.7 g DCC) was added, and this was followed by agitation for one night. To this mixture 0.5 ml (CH₃)₂N(CH₂)₃NH₂ was added, followed by shaking for 30 minutes, then the mixture was concentrated. The resulting residue was dissolved in 300 ml AcOEt; the resulting solution was washed with 4% aqueous NaHCO₃ and 10% aqueous citrate, after which it was dried with Na₂SO₄. The dried matter was concentrated, then the resulting residue was precipitated with ether and collected by filtration.

Yield: 10.9 g (94.4%).
m.p.: 117° to 119° C., Rf¹: 0.41.
$[\alpha]_D^{25}$: −7.7°(c=0.9, in DMF).
Elemental analysis (as $C_{64}H_{77}N_7O_{11}S$): Calculated: C, 66.70; H, 6.73; N, 8.51; S, 2.78. Found: C, 66.47; H, 6.75, N, 8.53; S, 2.84.

(IV) Production of Boc-Asn-Ser(Bzl)-Phe-Arg(Pme)-Tyr(Bzl)-Obzl 4.5 g Boc-Ser(Bzl)-Phe-Arg(Pme)-Tyr(Bzl)-OBzl was treated with TFA in the same manner as in Example 1-(I); the amine component thus obtained was dissolved in 50 ml DMF and cooled with ice, then 1.5 ml TEA was added. To this mixture Boc-Asn-ONB (prepared with 1.2 g Boc-Asn-OH, 1.0 g HONB and 1.2 g DCC) was added, and this was followed by agitation for one night. The mixture was then concentrated, and the resulting residue was precipitated with water and collected by filtration. The collected precipitate was dissolved in DMF, and insoluble matter was filtered, then the solution was concentrated. The resulting residue was precipitated with ether and collected by filtration.

Yield: 4.75 g (96.0%)

m.p.: 148° to 150° C., Rf$^1$: 0.18

$[\alpha]_D^{25}$: −21.0°(c=0.9, in DMF).

Elemental analysis (as $C_{68}H_{83}N_9O_{13}S$): Calculated: C, 63.93; H, 6.63; N, 9.87; S, 2.51. Found: C, 63.75; H, 6.66; N, 10.23; S, 2.58.

(V) Production of Boc-Cys(MBzl)-Asn-Ser(Bzl)-Phe-Arg(Pme)-Tyr(Bzl)-OBzl 4.6 g Boc-Asn-Ser(Bzl)-Phe-Arg(Pme)-Tyr(Bzl)-OBzl was treated with TFA in the same manner as in Example 1-(I); the amine component thus obtained was dissolved in 50 ml DMF and cooled with ice, then 0.9 ml TEA was added. To this mixture Boc-Cys(MBzl)-ONB (prepared with 2.0 g Boc-Cys(MBzl)-OH.CHA, 0.90 g HONB and 1.04 g DCC) was added, and this was followed by agitation for one night. The mixture was then concentrated, and the resulting residue was precipitated with ether and collected by filtration.

Yield: 5.25 g (96.9%)

m.p: 177° to 183° C., Rf$^{1b}$: 0.24.

$[\alpha]_D^{25}$: −18.6°(c=0.9, in DMF).

Elemental analysis (as $C_{79}H_{96}N_{10}O_{15}S_2 \cdot H_2O$): Calculated: C, 62.92; H, 6.55; N, 9.29; S, 4.25. Found: C, 62.92; H, 6.47; N, 9.35; S, 4.74.

(VI) Production of Boc-Leu-Gly-OBzl

To 20.2 g H-Gly-OBzl.p-Tos-OH 200 ml acetonitrile was added, and this mixture was followed by cooling with ice, then 8.4 ml TEA was added. To this mixture Boc-Leu-ONB (prepared with 11.6 g Boc-Leu-OH, 9.9 g HONB and 11.3 g DCC) was added, and this was followed by agitation for one night. The mixture was concentrated, then the resulting residue was dissolved in 300 ml AcOEt. The resulting solution was washed with 4% aqueous $NaHCO_3$ and 10% aqueous citrate, after which it was dried with $Na_2SO_4$. The dried matter was concentrated to obtain the desired product in the form of an oily substance.

Yield: 19.0 g (quantitative), Rf$^1$: 0.78.

(VII) Production of Boc-Gly-Leu-Gly-OBzl 16.1 g Boc-Leu-Gly-OBzl was treated with 50 ml TFA; the amine component thus obtained was dissolved in 150 ml DMF and cooled with ice, followed by neutralization with TEA. To this neutralized solution Boc-Gly-ONB (prepared with 5.3 g Boc-Gly-OH, 6.0 g HONB and 6.8 g DCC) was added, and this was followed by agitation for one night. The mixture was then concentrated, and the resulting residue was dissolved in 300 ml AcOEt. The resulting solution was washed with 4% aqueous $NaHCO_3$ and 10% aqueous citrate, after which it was dried with $Na_2SO_4$. The dried product was concentrated, after which it was crystallized with petroleum benzine and collected by filtration.

Yield: 13.0 g(quantitative).

m.p.: 110° to 111° C., Rf$^1$: 0.39.

$[\alpha]_D^{25}$: −13.4°(c=1.0, in DMF).

Elemental analysis (as $C_{22}H_{33}N_3O_6$): Calculated: C, 60.67; H, 7.64; N, 9.65. Found: C, 61.20; H, 7.32; N, 9.65.

(VIII) Production of Boc-Ser(Bzl)-Gly-Leu-Gly-OBzl 8.7 g Boc-Gly-Leu-Gly-OBzl was treated with TFA in the same manner as in example 1-(I); the amine component thus obtained was dissolved in 100 ml DMF and cooled with ice, then 3.3 ml TEA was added. To this mixture Boc-Ser(Bzl)-ONB (prepared with 6.3 g Boc-Ser(Bzl)-OH, 4.1 g HONB and 4.7 g DCC) was added, and this was followed by agitation for one night. To the mixture 2 ml $(CH_3)_2N(CH_2)_3NH_2$ was added, and this mixture was followed by shaking for 30 minutes. The mixture was then concentrated, and the resulting residue was dissolved in 300 ml AcOEt. The resulting solution was washed with 4% aqueous $NaHCO_3$ and 10% aqueous citrate, after which it was dried with $Na_2SO_4$. After concentration, the dried product was precipitated with ether-petroleum benzine and collected by filtration.

Yield: 9.6 g (78.3%).

m.p.: 79° to 81° C., Rf$^1$: 0.33.

$[\alpha]_D^{25}$: −12.0°(c=1.0, in DMF).

Elemental analysis (as $C_{32}H_{44}N_4O_8$): Calculated: C, 62.73; H, 7.24; N, 9.14. Found: C, 62.92; H, 7.52; N, 9.16.

(IX) Production of Boc-Gln-Ser(Bzl)Gly-Leu-Gly-OBzl 3.6 g Boc-Ser(Bzl)-Gly-Leu-Gly-OBzl was treated with TFA in the same manner as in Example 1-(I); the amine component thus obtained was dissolved in 40 ml DMF and cooled with ice, then 1.1 ml TEA was added. To this mixture Boc-Gln-ONB (prepared was 1.93 g Boc-Gln-OH, 1.55 g HONB and 1.77 g DCC) was added, and this was followed by agitation for one night. The mixture was then concentrated, and the resulting residue was precipitated with water and collected by filtration. The collected precipitate was again dissolved in DMF. The resulting solution, after filtering insoluble matter, was concentrated; the resulting residue was precipitated with ether and collected by filtration. The collected precipitate was washed with AcOEt and then acetonitrile.

Yield: 3.35 (76.9%).

m.p.: 182° to 184° C., Rf$^2$: 0.50.

$[\alpha]_D^{25}$: −11.3°(c≦1.0, in DMF).

Elemental analysis (as $C_{37}H_{52}N_6O_{10}$): Calculated: C, 59.99; H, 7.07; N, 11.34. Found: C, 59.98; H, 7.14; N, 11.44.

(X) Production of Boc-Ala-Gln-Ser(Bzl)-Gly-Leu-Gly-OBzl 3.2 g Boc-Gln-Ser(Bzl)-Gly-Leu-Gly-OBzl was treated with 25 ml TFA; the amine component thus obtained was dissolved in 30 ml DMF and cooled with ice, then 0.9 ml TEA was added. To this mixture Boc-Ala-ONB (prepared with 1.0 g Boc-Ala-OH, 1.05 g HONB and 1.20 g DCC) was added, and this was followed by agitation for 5 hours. This mixture was then concentrated; the resulting residue was precipitated with ether and collected by filtration.

Yield: 3.5 g (quantitative).

m.p.: 205° to 211° C. (decomposed), Rf$^2$: 0.44.

$[\alpha]_D^{25}$: −14.6°(c=0.9, in DMF).

Elemental analysis (as $C_{40}H_{57}N_7O_{11} \cdot \frac{1}{2}H_2O$): Calculated: c, 58.72; H, 7.12, N, 11.94. Found: C, 58.54; H, 6.90; N, 11.74.

(XI) Production of Boc-Ala-Gln-Ser-Gly-Leu-Gly-OH 1.50 g Boc-Ala-Gln-Ser(Bzl)-Gly-Leu-Gly-OBzl was dissolved in 100 ml AcOH and subjected to 8 hours of catalytic reduction in the presence of Pd-black as a catalyst. After filtering the catalyst, the reduced solution was concentrated; the resulting residue was precipitated with ether and collected by filtration.

Yield: 1.10 g (94.3%).
m.p.: 178° to 180° C. (decomposed), $Rf^3$: 0.14.
$[\alpha]_D^{25}$: $-15.3°$(c=0.9, in DMF).
Elemental analysis (as $C_{26}H_{45}N_7O_{11}$): Calculated: C, 49.44; H, 7.18; N, 15.52. Found: C, 49.14; H, 7.15; N, 15.52.

(XII) Production of Z-Ile-Gly-OBzl

To 8.0 g H-Gly-OBu$^t$.Hcl 200 ml acetonitrile was added, and this mixture was followed by cooling with ice, then 6.7 ml TEA was added. To this mixture Z-Ile-ONB (prepared with 14.6 g Z-Ile-OH, 11.0 g HONB and 12.5 g DCC) was added, and this was followed by agitation for one night. To the mixture 2.5 ml $(CH_3)_2N(CH_2)_3NH_2$ was added, and this was followed by shaking for 30 minutes. The mixture was then concentrated, and the resulting residue was dissolved in 300 ml AcOEt. The resulting solution was washed with 4% aqueous $NaHCO_3$ and 10% aqueous citrate, after which it was dried with $Na_2SO_4$. The dried product was concentrated; the resulting residue was crystallized with ether-petroleum benzine and collected by filtration.

Yield: 17.8 g (85.0%).
m.p.: 127° to 128° C. $Rf^2$: 0.81.
$[\alpha]_D^{25}$: $-4.5°$(c=1.1, in DMF).
Elemental analysis (as $C_{20}H_{30}N_2O_5$): Calculated: C, 63.47; H, 7.99; N, 7.40. Found: C, 63.56; H, 8.16; N, 7.47.

(XIII) Production of Boc-Arg(Pme)-Ile-Gly-OBu$^t$ 5.0 g Z-Ile-Gly-OBu$^t$ was reduced in the presence of Pd-black as a catalyst in 150 ml of MeOH; the amine component thus obtained was dissolved in 50 ml DMF. To the resulting solution were added 5.8 g Boc-Arg(Pme)-OH and 1.8 g HOBt, and this was followed by cooling with ice, then 2.8 g DCC was added, to be followed by agitation for one night. The resulting DCU was filtered, ad the filtrate was concentrated, then the resulting residue was dissolved in 200 ml AcOEt. The resulting solution was washed with 4% aqueous $NaHCO_3$ and 10% aqueous citrate, after which it was dried with $Na_2SO_4$. The dried product, after concentration, was crystallized with ether and collected by filtration.

Yield: 8.52 g (quantitative).
m.p.: 115° to 188° C., $Rf^1$: 0.32.
$[\alpha]_D^{25}$: $-10.4°$(c=1.0, in DMF).
Elemental analysis (as $C_{34}H_{58}N_6O_8S$): Calculated: C, 57.44; H, 8.22; N, 11.82; S, 4.51. Found: C, 58.24; H, 8.20; N, 11.68; S, 4.54.

(XIV) Production of Boc-Asp-(OBzl)-Arg(Pme)-Ile-Gly-OH.CHA 8.50 g Boc-Arc(Pme)-Ile-Gly-OBu$^t$ was dissolved in 60 ml TFA, and this mixture was followed by shaking at room temperature for 1 hour. The mixture, after concentration, was precipitated with ether and collected by filtration. The collected precipitate was dissolved in 100 ml DMF and cooled with ice, then 3.8 ml TEA was added. To the mixture Boc-Asp-(OBzl)-ONB (prepared with 4.85 g Boc-Asp(OBzl)-OH, 2.97 g HONB and 3.40 g DCC) was added, and this was followed by agitation for one night. The mixture, after concentration, was acidified with citric acid and extracted with 200 ml AcOEt. The resulting extract was washed with water, after which it was dried with $Na_2SO_4$. The dried product, after concentration, was precipitated with ether and collected by filtration. The collected precipitate was dissolved in AcOEt, then 1.1 ml CHA was added. The mixture was crystallized with ether and collected by filtration, and the collected crystal was recrystallized with acetonitrile.

Yield: 7.40 g (64.3%).
m.p.: 146° to 148° C., $Rf^2$: 0.43.
$[\alpha]_D^{25}$: $-4.2°$(c=1.1, in DMF).
Elemental analysis ($C_{47}H_{74}N_8O_{11}S$): Calculated: C, 58.85; H, 7.78; N, 11.68; S, 3.34. Found: C, 58.59; H, 7.74; N, 11.61; S, 3.50.

(XV) Production of Boc-Met-Asp(OBzl)-Arg(Pme)-Ile-Gly-OH 3.0 g Boc-Asp(OBzl)-Arg(Pme)-Ile-Gly-OH.CHA was suspended in 100 ml AcOEt. To the resulting suspension were added 4 ml of 1N-$H_2SO_4$ and 50 ml water, and this mixture was followed by shaking. The mixture was then washed with water, after which it was dried with $Na_2SO_4$. The dried product was concentrated, and the resulting residue was treated with 30 ml TFA. The amine component thus obtained was dissolved in 40 ml DMF and cooled with ice, then 0.9 ml TEA was added. To this mixture Boc-Met-ONB (prepared with 4.3 g Boc-Met-OH.DCHA, 2.0 g HONB and 2.3 g DCC) was added, and this was followed by agitation for one night. After adding 1 ml AcOH, the mixture was concentrated; the resulting residue was crystallized with AcOEt and collected by filtration.

Yield: 3.1 g (quantitative).
m.p.: 175° to 178° C., $Rf^2$: 0.41.
$[\alpha]_D^{25}$: $-11.2°$(c=1.0, in DMF).
Elemental analysis (as $C_{46}H_{70}N_8O_{12}S_2$): Calculated: C, 55.74; H, 7.12; N, 11.30; S, 6.47. Found: C, 55.95; H, 7.42; N, 11.26; S, 5.96.

(XVI) Production of Boc-Arg(Pme)-Met-Asp(OBzl)-Arg(Pme)-Ile-Gly-OH 2.6 g Boc-Met-Asp(OBzl)-Arg(Pme)-Ile-Gly-OH was treated with 20 ml TFA; the amine component thus obtained was dissolved in 50 ml DMF and cooled with ice, then 1 ml TEA was added. To this mixture Boc-Arg(Pme)-ONB (prepared with 1.52 g Boc-Arg(Pme)-OH, 1.62 g HONB and 0.71 g DCC) was added, and this was followed by agitation for one night. To this mixture 2 ml AcOH was added, and this was followed by concentration; the resulting concentrate was precipitated with AcOEt and collected by filtration.

Yield: 3.03 g (85.2%).
m.p.: 230° C. (decomposed), $Rf^2$: 0.37.
$[\alpha]_D^{25}$: $-10.2°$(c=0.2, in DMF).
Elemental analysis (as $C_{63}H_{96}N_{12}O_{15}S_3$): Calculated: C, 55.73; H, 7.13; N, 12.38; S, 7.09. Found: C, 56.33; H, 7.34; N, 12.17; S, 6.87.

(XVII) Production of Boc-Gly-Gly-OBzl

To 22.2 g H-Gly-OBzl.p-Tos-OH 200 ml acetonitrile was added, and this mixture was followed by cooling with ice, then 9.2 ml TEA was added. To this mixture Boc-Gly-ONB (prepared with 10.5 g Boc-Gly-OH, 11.9 g HONB and 13.6 DCC) was added, and this was followed by agitation for one night, then, after the addition of 1 ml $(CH_3)_2N(CH_2)_3NH_2$, the mixture was concentrated. The resulting residue was dissolved in 300 ml AcOEt, and the solution was washed with 4% aqueous NaHCO$_3$ and 10% aqueous citrate, after which it was dried with Na$_2$SO$_4$. The dried product was concentrated, and the resulting residue was crystallized with petroleum benzine and collected by filtration; the collected crystal was washed with ether.

Yield: 18.2 g (94.1%).
m.p.: 81° to 82° C., Rf$^1$: 0.53.
Elemental analysis (as D$_{16}$H$_{22}$N$_2$O$_5$): Calculated: C, 59.62; H, 6.88; N, 8.69. Found: C, 59.85; H, 6.96; N, 8.66.

(XVII) Production of Boc-Phe-Gly-Gly-OBzl 17.0 g Boc-Gly-Gly-OBzl was treated with 150 ml TFA; the amine component thus obtained was dissolved in 150 ml DMF, and this mixture was followed by cooling with ice and neutralization with TEA. To this solution Boc-Phe-ONB (prepared with 10.0 g Boc-Phe-OH, 7.5 g HONB and 8.6 g DCC) was added, and this was followed by agitation for one night. The mixture was then concentrated, and the resulting residue was dissolved in 300 ml AcOEt. The resulting solution was washed with 4% aqueous NaHCO$_3$ and 10% aqueous citrate, after which it was dried with Na$_2$SO$_4$. After concentrating the dried product, the resulting residue was crystallized with ether and collected by filtration.

Yield: 16.9 g (95.5%).
m.p.: 94° to 96° C., Rf$^1$: 0.41.
$[\alpha]_D^{25}$: −6.9°(c=1.0, in DMF).
Elemental analysis (as C$_{25}$H$_{31}$N$_3$O$_6$): Calculated: C, 63.95; H, 6.65; N, 8.95. Found: C, 63.96; H, 6.68; N, 9.20.

(XIX) Production of Boc-Phe-Gly-Gly-OH.CHA 7.0 g Boc-Phe-Gly-Gly-OBzl was reduced in the presence of Pd-black as a catalyst in 200 ml MeOH, and this was followed by concentration. The resulting concentrate, after the addition of 1.72 ml CHA, was crystalized with AcOEt and collected by filtration.

Yield: 6.90 g (96.1%).
m.p.: 159° to 161° C., Rf$^2$: 0.25.
$[\alpha]_D^{25}$: −10.1°(c=1.0, in DMF).
Elemental analysis (as C$_{24}$H$_{38}$N$_4$O$_6$): Calculated: C, 60.28; H, 8.00; N, 11.71. Found: C, 59.94; H, 7.99; N, 11.97.

(XX) Production of Boc-Cys(MBzl)-Phe-Gly-Gly-OH

Boc-Phe-Gly-Gly-OH (prepared with 6.9 g Boc-Phe-Gly-Gly-OH.CHA and 18 ml of 1N-H$_2$SO$_4$) was treated with TFA; the amine component thus obtained was dissolved in DMF, and this mixture was followed by cooling with ice, then 4.62 ml TEA was added. To this mixture Boc-Cys(MBzl)-ONB (prepared with 6.35 g Boc-Cys(MBzl)-OH.CHA, 2.88 g HONB and 3.30 g DCC) was added, and this was followed by agitation for 3 hours. The mixture, after adding 0.57 ml (CH$_3$)$_2$N(CH$_2$)$_3$NH$_2$, was concentrated, and the resulting residue was dissolved in 200 ml AcOEt. The resulting solution was washed with 4% aqueous NaHCO$_3$ and 10% aqueous citrate, after which it was dried with Na$_2$SO$_4$. The dried product, after concentration, was crystallized with ether and collected by filtration.

Yield: 6.0 g (69.1%).
m.p.: 120° to 122° C., Rf$^2$: 0.51.
$[\alpha]_D^{25}$: −19.8°(c=0.9, in DMF).
Elemental analysis (as C$_{29}$H$_{38}$N$_4$O$_8$S): Calculated: C, 57.79; H, 6.35; N, 9.30; S, 5.32. Found: C, 57.48; H, 6.63; N, 9.31; S, 4.89.

(XXI) Production of Boc-Aib-Cys(MBzl)-Phe-Gly-Gly-OH 300 mg Boc-Cys(MBzl)-Phe-Gly-Gly-OH was treated with 5 ml TFA; the amine component thus obtained was dissolved in 3 ml DMF, then 0.2 ml TEA was added. To this mixture Boc-Aib-ONB (prepared with 112 mg BOc-Aib-OH, 110 mg HONB and 124 mg DCC) was added, and this was followed by agitation for one night. The mixture, after the addition of 0.1 ml (CH$_3$)$_2$N(CH$_2$)$_3$NH$_2$, was concentrated, and the resulting residue was dissolved in AcOEt. The resulting mixture was washed with 4% aqueous NaHCO$_3$ and 10% aqueous citrate, after which it was dried with Na$_2$SO$_4$. The dried product was concentrated; the resulting residue was precipitated with ether and collected by filtration.

Yield: 240 mg (69.8%).
m.p.: 84° to 86° C., Rf$^2$: 0.34.
$[\alpha]_D^{25}$: −38.8°(c=1.0, in DMF).
Elemental analysis (as C$_{33}$H$_{34}$N$_5$O$_9$S): Calculated: C, 57.63; H, 6.59; N, 10.18; S, 4.66. Found: C 57.87; H, 6.95; N, 9.81; S, 4.76.

(XXII) Production of Boc-Ala-Gin-Ser-Gly-Leu-Gly-Cys(MBzl)-Asn-Ser(Bzl)-Phe-Arg(Pme)-Tyr(Bzl)-OBzl 500 mg Boc-Cys(MBzl)-Asn-Ser(Bzl)-Phe-Arg(Pme)-Tyr(Bzl)-OBzl was dissolved in 5 ml TFA, and this was followed by concentration; the resulting residue was precipitated with ether and collected by filtration. The collected precipitate was dissolved in 3 ml DMF, and this mixture was followed by cooling with ice, then 0.47 ml TEA was added, and this was followed by agitation. The mixture was then precipitated with ether and collected by filtration. The collected precipitate was dissolve din 5 ml DMF. To this solution were added 222 mg Boc-Ala-Gln-Ser-Gly-Leu-Gly-OH and 121 mg HONB, and this was followed by cooling with ice, then 138 mg DCC was added, to be followed by agitation for 3 days. The resulting DCU was filtered, and the resulting filtrate was concentrated. The resulting residue was precipitated with acetonitrile and collected by filtration; the collected precipitate was washed with hydrous acetonitrile.

Yield: 585 mg (87.1%)
m.p.: 235° to 237° C. (decomposed), Rf$^2$: 0.14.
$[\alpha]_D^{25}$: −18.4°(c=0.9, in DMF).
Elemental analysis as C$_{100}$H$_{131}$N$_{17}$O$_{23}$S$_2$): Calculated: C, 59.95; H, 6.59; N, 11.89; S, 3.20. Found: C, 60.00; H, 6.76; N, 11.83; S, 3.82.

(XXIII) Production of Boc-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 500 mg of the compound obtained in Example 1-(XXII), 357 mg Boc-Arg(Pme)-Met-Asp-OBzl)-Arg(Pme)-Ile-Gly-OH, 90 mg HONB and 309 mg DCC, the desired product was obtained in exactly the same manner as in Example 1-(XXII)

Yield: 680 mg (84.0%).
m.p.: 220° to 224° C., Rf$^2$: 0.29.
$[\alpha]_D^{25}$: −14.7°(c=0.9, in DMF).
Elemental analysis (as C$_{158}$H$_{217}$N$_{29}$O$_{35}$S$_5$): Calculated: C, 58.52; H, 6.75; N, 12.85; S, 4.94. Found: C, 58.82; H, 6.92; N, 12.23; S, 5.13.

(XXIV) Production of Boc-Aib-Cys(MBzl)-Phe-Gly-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXIII), 95 mg Boc-Aib-Cys(MBzl)-Phe-Gly-Gly-OH, 50 mg HONB and 167 mg DCC, the desired product was obtained in exactly the same manner as in Example 1-(XXII).

Yield: 20 mg (82.3%).
m.p.: 232° to 233° C. (decomposed).
Elemental analysis (as $C_{186}H_{252}N_{34}O_{41}S_6$): Calculated: C, 58.60; H, 6.66; N, 12.49; S, 5.05. Found: C, 58.48; H, 7.14; N, 12.28; S, 4.62.

(XXV) Production of H—Aib—Cys—Phe—Gly—Gly—Arg—Met—Asp—Arg—Ile—Gly—Ala—Gln—Ser—Gly—Leu—Gly—Cys—Asn—Ser—Phe—Arg—Tyr—OH([Aib6]-α-hANP[6-28])

To 200 mg of the compound obtained in Example 1-(XXIV) were added 0.3 ml anisole, 0.3 ml thioanisole and 3 ml HF, and this was followed by agitation at 0° C. for 60 minutes, then the mixture was concentrated. The resulting residue was precipitated with ether, and the ether layer was removed by decantation. The resulting residue was dissolved in 10 ml water, followed by ion exchange through a column (1×10 cm) of Amberlite IRA-400 (Rohm and Haas Co., USA, acetate type). The solution was then diluted with water to a volume of 1 l and adjusted to pH 6.9 with aqueous $C-NH_3$. The diluted solution, after the addition of 500 mg $AcONH_4$, was oxidized with air at room temperature for 4 hours, and this was followed by lyophilization. The lyophilized product was subjected to elution with 1N aqueous AcOH through a column of Sephadex LH-20 (2.6×130 cm); 263 to 305 ml of a fraction was collected and lyophilized. Yield: 16 mg (12%)

Amino acid analysis: Asp 2.03, Ser 1.89, Glu 1.03, Gly 5.04, Ala 1.01, Half Cys 1.82, Met 1.00, Ile 1.00, Leu 1.00 Tyr 0.90, Phe 1.96, Arg 3.06, Aib 0.97.

EXAMPLE 2

Production of [Achc6]-α-hANP[6-28]

(I) Production of Boc-Achc-OH 2.0 g of 1-amino-1cyclohexanecarboxylic acid was suspended in dioxane-water (5 ml-5 ml), and 3 ml TEA was added. To this mixture 3.8 g Boc-ON was added, and this was followed by agitation for 2 days. The mixture was then concentrated; the resulting concentrate, after adding water, was washed with ether. The water layer was cooled with ice and acidified with HCl, after which it was extracted with AcOEt; the resulting extract, after washing with water, was dried with $Na_2SO_4$. The dried product was concentrated; the resulting residue was crystallized with petroleum benzine and collected by filtration.

Yield: 0.60 g (17.6%).
m.p.: 173° top 175° C., $Rf^2$: 0.51.
Elemental analysis (as $C_{12}H_{21}NO_4$): Calculated: C, 59.24; H, 8.70; N, 5.76. Found: C, 59.04; H, 8.87; N, 5.64.

(II) Production of Boc-Achc-Cys(MBzl)Phe-Gly-Gly-OH

Using 300 mg Boc-Cys(MBzl)-Phe-Gly-Gly-OH, 134 mg Boc-Achc-OH, 108 mg HONB and 124 mg DCC, the desired product was obtained in exactly the same manner as in Example 1-(XXI).

Yield: 202 mg (54.9%).
m.p.: 74° to 77° C., $Rf^2$: 0.40.
$[\alpha]_D^{25}$: −30.7°(c=1.2, in DMF).

Elemental analysis (as $C_{36}H_{49}N_5O_9S$): Calculated: C, 59.40; H, 6.79; N, 9.62; S, 4.41. Found: C, 59.87; H, 7.19; N, 9.39; S, 4.69.

(III) Production of Boc-Achc-Cys-MBzl)-Phe-Gly-Gly-Arg(Pme)-Met-Asp(Obzl)-Arg(Pme)Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXIII), 101 mg Boc-Achc-Cys(MBzl)-Phe-Gly-Gly-OH, 50 mg HONB and 167 mg DCC, the desired production was obtained in exactly the same manner as in Example 1-(XXII).

Yield: 301 mg (84.5%).
m.p.: 235° to 240° C. (decomposed).
Elemental analysis ($C_{189}H_{256}N_{34}O_{41}S_6$): Calculated: C, 58.92, H, 6.70; N, 12.36; S, 4.99. Found: C, 58.68, H, 7.11; N, 12.07; S, 4.66.

(IV) Production of H—Achc—Cys—Phe—Gly—Gly—Arg—Met—Asp—Arg—Ile—Gly—Ala—Gln—Ser—Gly—Leu—Gly—Cys—Asn—Ser—Phe—Arg—Tyr—OH([Achc6]-α-hANP[6-28])

Using 200 mg of the compound obtained in Example 2-(III), the desired product was obtained via HF treatment, air oxidation and purification in exactly the same manner as in Example 1-(XXV). Yield: 30 mg (22%)

Amino acid analysis: Asp 2.04, Ser 1.87, Glu 1.06, Gly 5.03, Ala 1.00, Half Cys 1.80, Met 0.99, Ile 1.00, Leu 1.01, Tyr 0.91, Phe 1.94, Arg 3.09, Achc 1.05.

EXAMPLE 3

Production of [D-Ala9]-α-hANP[7-28]

(I) Production of Boc-D-Ala-Gly-OBzl

To 7.4 g H-Gly-OBzl.p-Tos-OH, 100 ml acetonitrile was added, and this was followed by cooling with ice, then 3.1 ml TEA, 3.78 g Boc-D-Ala-OH, 3.96 g HONB and 4.54 g DCC were added, and this was followed by agitation for one night. The resulting DCU was filtered, and the filtrate was concentrated, then the resulting residue was dissolved in 300 ml AcOEt. The resulting solution was washed with 4% aqueous NaHCO$_3$ and 10% aqueous citrate, after which it was dried with Na$_2$SO$_4$. The dried product, after concentration, was crystallized with petroleum benzine and collected by filtration.

Yield: 6.70 g (quantitative)
m.p.: 77° to 78° C., Rf$^2$: 0.66.
$[\alpha]_D^{25}$: +10.5°(c=0.9, in DMF).
Elemental analysis (as C$_{17}$H$_{24}$N$_2$O$_5$): Calculated: C, 60.70; H, 7.19; N, 8.33. Found: C, 61.08; H, 7.21; N, 8.07.

(II) Production of Boc-Phe-D-Ala-Gly-OBzl 3.70 g Boc-D-Ala-Gly-OBzl was dissolved in 30 ml TFA, and this was followed by concentration; the resulting residue was dissolved in 40 ml acetonitrile and cooled with ice, and this was followed by neutralization with TEA. To this solution, 4.26 g Boc-Phe-ONB was added, and this mixture was followed by agitation for one night. The mixture was then concentrated, and the resulting residue was dissolved in 200 ml AcOEt. The resulting solution was washed with 4% aqueous NaHCO$_3$ and 10% aqueous citrate, after which it was dried with Na$_2$SO$_4$. The dried product was concentrated; the resulting residue was precipitated with ether and collected by filtration.

Yield: 4.25 g (87.9%).
m.p.: 127° to 129° C., Rf$^2$: 0.60.
$[\alpha]_D^{25}$: −0.5°(c=0.9, in DMF).
Elemental analysis (as C$_{26}$H$_{33}$N$_3$O$_6$): Calculated: C, 64.58; H, 6.88; N, 8.69. Found: C, 64.45; H, 7.07; N, 8.78.

(III) Production of Boc-Cys(MBzl)-Phe-D-Ala-Gly-OH 0.48 g Boc-Phe-D-Ala-Gly-OBzl was reduced in 50 ml MeOH in the presence of Pd-black as a catalyst. The reduced product was concentrated; the resulting residue was dissolved in 5 ml TFA, followed by concentration. The resulting concentrate was precipitated with ether and collected by filtration. The collected precipitate was dissolved in 5 ml DMF, and this was followed by cooling with ice. To this solution 0.35 ml TEA was added, then Boc-Cys(MBzl)-ONB (prepared with 0.48 g Boc-Cys(MBzl)-OH-CHA, 0.22 g HONB and 0.25 g DCC) was added, and this mixture was followed by agitation for one night. To this mixture 0.2 ml (CH$_3$)$_2$N(CH$_2$)$_3$NH$_2$ was added, and the mixture was concentrated, and the resulting residue was dissolved in 50 ml AcOEt. The resulting solution was washed with 4% aqueous NaHCO$_3$ and 10% aqueous citrate, after which it was dried with Na$_2$SO$_4$. The dried product was concentrated; the resulting residue was precipitated with ether and collected by filtration. The collected precipitate was eluted with the solvent CHCl$_3$-MeOH-AcOH (9:0.5:0.2) through a silica gel column (25 g silica gel); the fraction containing the desired product was collected and concentrated. The resulting concentrate was precipitated with ether and collected by filtration.

Yield: 0.24 g (38.9%).

m.p.: 104° to 107° C., Rf$^2$: 0.49.
$[\alpha]_D^{25}$: −6.0°(c=0.9, in DMF).
Elemental analysis (as C$_{30}$H$_{40}$N$_4$O$_8$S): Calculated: C, 58.43; H, 6.54; N, 9.08; S, 5.20. Found: C, 58.57; H, 6.66; N, 9.16; S, 5.17.

(IV) Production of
Boc-Cys(MBzl)-Phe-D-Ala-Gly-Arg(Pme)-Met-Asp(OBzl)-Arg(Pme)-Ile-Gly-Ala-Gln-Ser-Gly-Leu-Gly-Cys(MBzl)-Asn-Ser-Phe-Arg(Pme)-Tyr(Bzl)-OBzl Using 300 mg of the compound obtained in Example 1-(XXIII), 86 mg Boc-Cys(MBzl)-Phe-D-Ala-Gly-OH, 50 mg HONG and 167 mg DCC, the desired product was obtained in exactly the same manner as in Example 1-(XXII)

Yield: 290 mg (83.8%).
m.p.: 235° to 240° C. (decomposed).
Elemental analysis (as C$_{183}$H$_{247}$N$_{33}$O$_{40}$S$_6$): Calculated: C, 58.74; H, 6.65; N, 12.36; S, 5.14. Found: C, 58.77; H, 7.03; N, 12.54; S, 4.81.

(V) Production of H—Cys—Phe—D—Ala—Gly—Arg—Met—Asp—Arg—Ile—Gly—Ala—Gln—Ser—Gly—Leu—Gly—Cys—Asn—Ser—Phe—Arg—Tyr—OH([D—Ala$^9$]-α-hANP[7-28])

Using 200 mg of the compound obtained in Example 3-(IV), the desired product was obtained via HF treatment, air oxidation and purification in exactly the same manner as in Example 1-(XXV).

Yield: 22 mg (16%).
Amino acid analysis: Asp 2.08, Ser 1.94, Glu 1.08, Gly 4.07, Ala 2.02, Half Cys 1.43, Met 0.85, Ile 1.00, Leu 1.03, Tyr 0.83, Phe 1.95, Arg 3.08.

EXAMPLE 4

Production of [Ava$^9$, des Gly$^{10}$]-α-hANP[7-28]

(I) Production of Boc-Phe-Ava-OBzl 6.3 g H-Ava-OBzl.p-Tos-OH was dissolved in 50 ml DMF, and this was followed by cooling with ice, then 3.5 ml TEA was added. To this mixture Boc-Phe-ONB (prepared with 4.0 g Boc-Phe-OH, 3.0 g HONB and 3.4 g DCC) was added, and this was followed by agitation for one night. To the mixture 1 ml (CH$_3$)$_2$N(CH$_2$)$_3$NH$_2$ was added, followed by concentration, then the resulting residue was dissolved in 200 ml AcOEt. The resulting solution was washed with 4% aqueous NaHCO$_3$ and 10% aqueous citrate, after which it was dried with Na$_2$SO$_4$. The dried product was concentrated; the resulting residue was crystallized with petroleum benzine, collected by filtration and dried.

Yield: 6.8 g (quantitative).
m.p.: 89° to 90° C., Rf$^2$: 0.66.
$[\alpha]_D^{25}$: −2.7°(c=0.9, in DMF).
Elemental analysis (as C$_{26}$H$_{34}$N$_2$O$_5$): Calculated: C, 68.70; H, 7.54; N, 6.16. Found: C, 68.65; H, 7.50; N, 6.40.

(II) Production of Boc-Phe-Ava-Oh 2.0 g Boc-Phe-Ava-OBzl was reduced in 50 ml MeOH in the presence of Pd-black as a catalyst, and this was followed by concentration. The resulting residue was crystallized with petroleum benzine and collected by filtration.

Yield: 1.50 g (94.6%).

m.p.: 111° to 112° C., Rf$^2$: 0.57.

[α]$_D^{25}$: −3.3°(c=1.2, in DMF).

Elemental analysis (as C$_{19}$H$_{28}$N$_2$O$_5$): Calculated: C, 62.62; H, 7.74; N, 7.69. Found: C, 62.75; H, 7.84; N, 7.78.

(III) Production of Boc-Cys(MBzl)-Phe-Ava-OH.CHA

Using 1.00 g Boc-Phe-Ava-OH, 1.32 g Boc-Cys(MBzl)-OH.CHA, 0.60 g NONB and 0.68 g DCC, the desired product was obtained in exactly the same manner as in Example 1-(XX), and was then dissolved in AcOEt-ether, after which it was crystallized with 0.2 ml CHA and collected by filtration.

Yield: 1.15 g (60.6%).

m.p.: 111° to 113° C., Rf$^2$: 0.61.

[α]$_D^{25}$: −21.7°(c=0.9, in DMF).

Elemental analysis (as C$_{36}$H$_{54}$N$_4$O$_7$S): Calculated: C, 62.94; H, 7.92; N, 8.16; S, 4.67. Found: C, 63.11; H, 7.93; N, 8.19; S, 4.63.

(IV) Production of
Boc-Cys(MBzl)-Phe-Ava-Arg(Pme)-Met-Asp(OBzl)-Arg(Pme)-Ile-Gly-Ala-Gln-Ser-Gly-Leu-Cys(MBzl)-Asn-Ser(Bzl)-Phe-Arg(Pme)-Tyr(Bzl)-OBzl Using 300 mg of the compound obtained in Example 1-(XXIII), Boc-Cys(MBzl)-Phe-Ava-OH (prepared with 96 mg of the corresponding CHA salt), 50 mg HONB and 167 mg DCC, the desired product was obtained in exactly the same manner as in Example 1-(XXII).

Yield: 325 mg (97.3%).

m.p.: 230° to 233° C. (decomposed).

Elemental analysis a(as C$_{177}$H$_{235}$N$_{31}$O$_{39}$S$_6$): Calculated: C, 58.83; H, 6.56; N, 12.02; S, 5.32. Found: C, 58.86; H, 7.01; N, 12.01; S, 4.84.

concentrated, and the resulting residue was dissolved in 200 ml AcOEt. The resulting solution was washed with 4% aqueous NaHCO$_3$ and 10% aqueous citrate, after which it was dried with Na$_2$SO$_4$. The dried product was concentrated; the resulting residue was crystallized with ether and collected by filtration.

Yield: 7.15 g (81.2%).

m.p.: 94° to 95° C., Rf$^1$: 0.66.

[α]$_D^{25}$: −2.9°(c=1.0, in DMF).

Elemental analysis (as C$_{25}$H$_{32}$N$_2$O$_5$): Calculated: C, 68.16; H, 7.32; N, 6.36. Found: C, 68.13; H, 7.50; N, 6.55.

(II) Production of Boc-Phe-Gaba-OH 3.0 g Boc-Phe-Gaba-OBzl was reduced in 50 ml MeOH in the presence of Pd-black as a catalyst, and this was followed by concentration. The resulting residue was crystallized with ether and collected by filtration.

Yield: 2.1 g (88.0%).

m.p.: 133° to 134° C., Rf$^1$: 0.14.

[α]$_D^{25}$: −4.0°(c=1.0, in DMF)

Elemental analysis (as C$_{18}$H$_{26}$N$_2$O$_5$): Calculated: C, 61.70; H, 7.48; N, 7.99. Found: C, 61.85; H, 7.66; N, 8.15.

(III) Production of Boc-Cys(MBzl)-Phe-Gaba-OH

Using 1.05 g Boc-Phe-Gaba-OH, 1.02 g Boc-Cys(MBzl)-OH, 0.60 g HONB and 0.68 g DCC, the desired product was obtained in exactly the same manner as in Example 1-(XX), and was then crystallized with ether and collected by filtration.

Yield: 1.05 g (61.02%).

m.p.: 103° to 104° C., Rf$^1$: 0.16.

[α]$_D^{25}$: −24.5°(c=1.1, in DMF).

Elemental analysis (as C$_{29}$H$_{39}$N$_3$O$_7$S): Calculated: C, 60.71; H, 6.85; N, 7.32; S, 5.59. Found: C, 60.94; H, 6.99;

(V) Production of H—Cys—Phe—Ava—Arg—Met—Asp—Arg—Ile—Gly—Ala—Gln—Ser—Gly—Leu—Gly—Cys—Asn—Ser—Phe—Arg—Tyr—OH([Ava$^9$, des Gly$^{10}$]-α-hANP[7-28])

Using 200 mg of the compound obtained in Example 4-(IV), the desired product was obtained via HF treatment, air oxidation and purification in exactly the same manner as in example 1-(XXV).

Yield: 41 mg (30%).

Amino acid analysis: asp 2.10, Ser 2.01, Glu 1.11, Gly 3.16, Ala 1.05, Half Cys 1.80, Met 0.99, Ile 1.00, Leu 1.06, Tyr 0.92, Phe 1.92, Arg 3.13, Ava 0.96.

EXAMPLE 5

Production of [Gaba$^9$, des Gly$^{10}$]-α-hANP[7-28]

(I) Production of Boc-Phe-Gaba-OBzl 8.77 g H-Gaba-OBzl-p-Tos-OH was suspended in 100 ml acetonitrile, and this was followed by cooling with ice, then 3.36 ml TEA was added. To this mixture, Boc-Phe-ONB (prepared with 5.3 g Boc-Phe-OH, 4.0 g HONB and 4.5 g DCC) was added, and this was followed by agitation for one night. This mixture was then

N, 7.44; S, 5.44.

(IV) Production of
Boc-Cys(MBzl)-Phe-Gaba-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 283 mg of the compound obtained in Example 1-(XXIII), 60 mg Boc-Cys(MBzl)-Phe-Gaba-OH, 38 mg HONB and 130 mg DCC, the desired product was obtained in exactly the same manner as in Example 1-(XXII).

Yield: 246 mg (78.4%).

Elemental analysis (as C$_{176}$H$_{233}$N$_{31}$O$_{39}$S$_6$): Calculated: C, 58.73, H, 6.53; N, 12.06; S, 5.35. Found: C, 59.06; H, 6.74; N, 11.89; S, 5.14.

(V) Production of H—Cys—Phe—Gaba—Arg—Met—Asp—Arg—Ile—Gly—Ala—Gln—Ser—Gly—Leu—Gly—Cys—Asn—Ser—Phe—Arg—Tyr—OH([Gaba$^9$, des Gly$^{10}$]-α-hANP[7-28])

Using 200 mg of the compound obtained in Example 5-(IV), the desired product was obtained via HF treatment, air oxidation and purification in exactly the same manner as in Example 1-(XXV).
Yield: 27 mg (20%).

Amino acid analysis: Asp 2.03, Ser 1.86, Glu 1.05, Gly 3.03, Ala 1.00, Half Cys 1.84, Met 0.98, Ile 1.00, Leu 0.99, Tyr 0.92, Phe 1.97, Arg 3.04, Gaba 1.01.

EXAMPLE 6

Production of [βAla⁹, des Gly¹⁰]-α-hANP[7-28]

(I) Production of Boc-Phe-βAla-OBzl

Using 8.43 g H-βAla-OBzl.p-Tos-OH, 3.36 ml TEA, 5.3 g Boc-Phe-OH, 4.0 g HONB and 4.5 g DCC, the desired product was obtained in exactly the same manner as in Example 5-(I), and was then crystallized with ether and collected by filtration.
Yield: 4.15 g (48.7%).
m.p.P 96° to 97° C., Rf¹: 0.66.
$[\alpha]_D^{25}$: −2.0°(c=1.1, in DMF).
Elemental analysis (as $C_{24}H_{30}N_2O_5$): Calculated: C, 67.59, H, 7.09; N, 6.57. Found: C, 67.38; H, 7.07; N, 6.65.

(II) Production of Boc-Phe-βAla-OH.CHA 3.0 g Boc-Phe-βAla-OBzl was reduced in 50 ml MeOH in the presence of Pd-black as a catalyst, and this was followed by concentration; the resulting residue was dissolved in 30 ml AcOEt, after which it was crystallized with 0.80 ml CHA and collected by filtration.
Yield: 3.0 g (98.0%).
m.p.: 155° to 165° C, Rf¹: 0.06.
$[\alpha]_D^{25}$: −4.4°(c=1.0, in DMF).
Elemental analysis (as $C_{23}H_{37}N_3O_5$): Calculated: C, 63.42; H, 8.56; N, 9.65. Found: C, 63.42; H, 8.56; N, 9.51.

(III) Production of Boc-Cys(MBzl)-Phe-βAla-OH

Using Boc-Phe-βAla-OH (prepared with 1.31 g Boc-Phe-βAla-OH.CHA), 1.02 g Boc-Cys(MBzl)-OH, 0.60 g HONB and 0.68 g DCC, the desired product was obtained in exactly the same manner as in Example 1-(XX), and was then crystallized with ether and collected by filtration.
Yield: 1.22 g (72.7%).
m.p.: 149° to 150° C., Rf¹: 0.13.
$[\alpha]_D^{25}$: −20.3°(c=1.0, in DMF).
Elemental analysis (as $C_{28}H_{37}N_3O_7S$): Calculated: C, 60.09; H, 6.66; N, 7.51; S, 5.73. Found: C, 60.33; H, 6.79; N, 7.80; S, 5.46.

(IV) Production of Boc-Cys(MBzl)-Phe-βAla-Arg(Pme)-Met-Asp(OBzl)-Arg(PME)-Ile-Gly-Ala-Gln-Ser-Gly-Leu-Gly-Cys(MBzl)-Asn-Ser(Bzl)-Phe-Arg(Pme)-Tyr(Bzl)-OBzl Using 283 mg of the compound obtained in Example 1-(XXIII), 59 mg Boc-Cys(MBzl)-Phe-βAla-OH, 38 mg HONB and 130 mg DCC, the desired product was obtained in exactly the same manner as in Example 1-(XXII).
Yield: 294 mg (94.0%).

Elemental analysis (as $C_{175}H_{231}N_{31}O_{39}S_6$): Calculated: C, 58.62; H, 6.49; N, 12.11; S, 5.37. Found: C, 58.95; H, 6.73; N, 11.95; S, 5.18.

(V) Production of H—Cys—Phe—βAla—Arg—Met—Asp—Arg—Ile—Gly—Ala—Gln—Ser—Gly—Leu—Gly—Cys—Asn—Ser—Phe—Arg—Tyr—OH([βAla⁹, des Gly¹⁰]-α-hANP[7-28])

Using 200 mg of the compound obtained in Example 6-(IV), the desired product was obtained via HF treatment, air oxidation and purification in exactly the same manner as in Example 1-(XXV).
Yield: 23 mg (17%).
Amino acid analysis: Asp 2.01, Ser 1.85, Glu 1.03, Gly 3.07, Ala 1.01, Half Cys 1.82, Met 0.99, Ile 1.00, Leu 1.01, Tyr 0.89, Phe 1.95, Arg 3.02, βAla 1.02.

EXAMPLE 7

Production of [des Gly⁹]-α-hANP[7-28])

(I) Production of Boc-Gly-Arg(Pme)-Met-Asp(OBzl)-Arg(Pme)-Ile-Gly-OH 1.0 g Boc-Arg(Pme)-Met-Asp(Bzl)-Arg(Pme)-Ile-Gly-OH was treated with 10 ml TFA; the amine component thus obtained was dissolved in 10 ml DMF, and this was followed by cooling with ice, then 0.25 ml TEA was added. To this solution 280 mg Boc-Gly-ONB was added, and this was followed by agitation for one night. To the mixture 1 ml AcOH was added, and this mixture was followed by concentration; the resulting residue was precipitated with AcOEt and collected by filtration.
Yield: 0.99 g (94.8%).
m.p.: 176° to 180° C., Rf²: 0.37.
$[\alpha]_D^{25}$: −11.4°(c=1.1, in DMF).
Elemental analysis (as $C_{65}H_{99}N_{13}O_{16}S_3$): Calculated: C, 55.18; H, 7.05; N, 12.87; S, 6.80. Found: C, 55.41; H, 7.43; N, 12.48; S, 6.30.

(II) Production of Boc-Phe-Gly-Arg(Pme)-Met-Asp(OBzl)-Arg(Pme)-Ile-Gly-OH

Using 400 mg Boc-Gly-Arg(Pme)-Met-Asp(OBzl)-Arg(Pme)-Ile-Gly-OH and 134 mg Boc-Phe-ONB, the desired product was obtained in exactly the same manner as in Example 7-(I), and was then washed with acetonitrile.
Yield: 337 mg (76.3%).
m.p.: 176° to 180° C., Rf²: 0.38.
$[\alpha]_D^{25}$: −12.6°(c=0.8, in DMF).
Elemental analysis (as $C_{74}H_{108}N_{14}O_{17}S_3$): Calculated: C, 56.90; H 6.97; N, 12.55; S, 6.16. Found: C, 56.92; H 7.44; N, 12.376; S, 5.83.

(III) Production of Boc-Cys(MBzl)-Phe-Gly-Arg(Pme)-Met-Asp(OBzl)-Arg(Pme)-Ile-Gly-OH Using 270 mg Boc-Phe-Gly-Arg(Pme)-Met-Asp(OBzl)-Arg(Pme)-Ile-Gly-OH and Boc-Cys(MBzl)-ONB (prepared with 65 mg Boc-Cys(MBzl)-OH, 38 mg HONB and 43 mg DCC), the desired product was obtained in exactly the same manner as in Example 7-(I), and was then washed with acetonitrile.
Yield: 240 mg (77.7%).

m.p.: 192° to 195° C., Rf$^2$: 0.41.
[α]$_D^{25}$: −14.8°(c=0.6, in DMF).
Elemental analysis (as C$_{85}$H$_{121}$N$_{15}$O$_{19}$S$_4$.3/2H$_2$O):
Calculated: C, 56,33; H, 6.90; N 11.59; S, 7.08. Found:
C, 56.33; H, 6.77; N, 11.77; S, 6.87.

(IV) Production of Boc-Cys(MBzl)-Phe-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 200 mg of the compound obtained in Example 1-(XXII), 196 mg Boc-Cys(MBzl)-Phe-Gly-Arg(Pme)-Met-Asp(OBzl)-Arg(Pme)-Ile-Gly-OH, 36 mg HONB and 82 mg DCC, the desired product was obtained in exactly the same manner as in Example 1-(XXII).
Yield: 289 mg (78.0%).
m.p.: 235° to 237° C. (decomposed).
Elemental analysis (as C$_{180}$H$_{2452}$N$_{32}$O$_{39}$S$_6$.2H$_2$O):
Calculated: C, 58.33; H, 6.69; N, 12.09; S, 5.19. Found:
C, 58.25; H, 6.96; N, 12.18; S, 5.00.

the desired product was obtained in exactly the same manner as in Example 1-(XVI).
Yield: 0.33 g (61.6%).
m.p.: 182° to 184° C., Rf$^2$: 0.51.
[α]$_D^{25}$: −9.8°(c=1.0, in DMF).
Elemental analysis (as C$_{64}$H$_{98}$N$_2$O$_{15}$S$_2$): Calculated:
C, 57.38; H, 7.37; N, 12.55; S, 4.79. Found: C, 57.25; H, 7.62; N, 12.17; S, 4.86.

(III) Production of Boc-Arg(Pme)-Ile-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXII), 221 mg Boc-Arg(Pme)-Ile-Asp(OBzl)-Arg(Pme)-Ile-Gly-OH, 60 mg HONB and 200 mg DCC, the desired product was obtained in exactly the same manner as in Example 1-(XXII).
Yield: 0.41 g (84.7%).
m.p.: 210° to 215° C., Rf$^2$: 0.52.
[α]$_D^{25}$: −15.0°(c=0.8, in DMF).

(V) Production of H—Cys—Phe—Gly—Arg—Met—Asp—Arg—Ile—Gly—Ala—Gln—Ser—Gly—Leu—Gly—Cys—Asn—Ser—Phe—Arg—Tyr—OH([des Gly$^9$]-α-hANP[7-28])
(disulfide bond between the two Cys residues)

Using 200 mg of the compound obtained in Example 7-(IV), the desired product was obtained via HF treatment, air oxidation and purification in exactly the same manner as in Example 1-(XXV).
Yield: 24 mg (18%).
Amino acid analysis: Asp 2.05, Ser 1.92, Glu 1.06, Gly 4.12, Ala 1.01, Half Cys 1.85, Met 0.99, Ile 1.00, Leu 1.01, Tyr 0.92, Phe 1.98, Arg 3.03.

EXAMPLE 8

Production of [Aib$^6$, Ile$^{12}$]-α-hANP[6-28]

(I) Production of Boc-Ile-Asp(OBzl)-Arg(Pme)-Ile-Gly-OH

Using 1.0 g Boc-Asp(OBzl)-Arg(Pme)-Ile-Gly-OH.CHA and Boc-Ile-ONB (prepared with 276 mg Boc-Ile-OH.½H$_2$O, 230 mg HONB and 262 mg DCC), the desired product was obtained in exactly the same manner as in Example 1-(XV).
Yield: 0.83 g (82.0%).
m.p.: 176° to 178° C., Rf$^2$: 0.47.
[α]$_D^{25}$: −16.0°(c=0.6, in DMF).
Elemental analysis (as C$_{47}$H$_{72}$N$_8$O$_{12}$S.H$_2$O): Calculated: C, 56.95; H, 7.52; N, 11.30; S, 3.24. Found: C, 57.11; H, 7.34; N, 11.41; S, 3.07.

(II) Production of Boc-Arg(Pme)-Ile-Asp(OBzl)-Arg(Pme)-Ile-Gly-OH

Using 0.39 g Boc-Ile-Asp(OBzl)-Arg(Pme)-Ile-Gly-OH and Boc-Arg(Pme)-ONB (prepared with 0.21 g Boc-Arg(Pme)-OH, 90 mg HONB and 100 mg DCC), Elemental analysis (as C$_{159}$H$_{219}$N$_{29}$O$_{35}$S$_4$): Calculated: C, 59.22; H, 6.84; N, 12.60; S, 3.98. Found: C, 58,89; H, 7.02; N, 12.51; S, 4.17.

(IV) Production of Boc-Aib-Cys(MBzl)-Phe-Gly-Gly-Arg(Pme)-Ile-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 500 mg of the compound obtained in Example 8-(III), 160 mg Boc-Aib-Cys(MBzl)-Phe-Gly-Gly-OH, 83 mg HONB and 288 mg DCC, the desired product was obtained in exactly the same manner as in Example 1-(XXII).
Yield: 409 mg (69.2%)
m.p.: 230° to 233° C. (decomposed).
Elemental analysis (as C$_{187}$H$_{254}$N$_{34}$O$_{41}$S$_5$): Calculated: C, 59.19; H, 6.75; N, 12.55; S, 4.22. Found: C, 59.39; H, 7.14; N, 12.40; S, 4.24.

(V) Production of H—Aib—Cys—Phe—Gly—Gly—Arg—Ile—Asp—Arg—Ile—Gly—Ala—Gln—Ser—Gly—Leu—Gly—Cys—Asn—Ser—Phe—Arg—Tyr—OH([Aib$^6$, Ile$^{12}$]-α-hANP[6-28])
(disulfide bond between the two Cys residues)

Using 200 mg of the compound obtained in Example 8-(IV), the desired product was obtained via HF treatment, air oxidation and purification in exactly the same manner as in Example 1-(XXV).
Yield: 25 mg (18%).
Amino acid analysis: Asp 2.02, Ser 1.85, Glu 1.05, Gly 5.06, Ala 1.01, Half Cys 1.79, Ile 2.00, Leu 0.99, Tyr 0.92, Phe 1.99, Arg 3.05, Aib 1.01.

EXAMPLE 9

Production of [D-Arg$^{27}$]-α-hANP[7-28]

(I) Production of Boc-D-Arg(Tos)-Tyr(Bzl)-OBzl

Using 2.32 g Boc-Tyr(Bzl)-OBzl, 2.37 g Boc-D-Arg(Tos)-OH, 0.75 g HONB and 1.14 g DCC, the desired product was obtained in exactly the same manner as in Example 1-(I).

Yield: 3.9 g (quantitative).
m.p.: 66° to 69° C., Rf$^1$: 0.30.
[α]$_D^{25}$: −7.8°(c=1.0, in DMF).
Elemental analysis (as C$_{41}$H$_{49}$N$_5$O$_8$S): Calculated: C, 63.79; H, 6.40; N, 9.07; S, 4.15. Found: C, 64.18; H, 6.54; N, 8.77; S, 4.13.

(II) Production of Boc-Phe-D-Arg(Tos)-Tyr(Bzl)-OBzl

Using 3.7 g Boc-D-Arg(Tos)-Tyr(Bzl)-OBzl, 1.40 g Boc-Phe-OH, 1.05 g HONB and 1.20 g DCC, the desired product was obtained in exactly the same manner as in Example 1-(II).

Yield: 4.10 g (93.0%).
m.p.: 78° to 80° C., Rf$^1$: 0.30.
[α]$_D^{25}$: −6.0°(c=1.0, in DMF).
Elemental analysis (as C$_{50}$H$_{58}$N$_6$O$_9$S): Calculated: C, 65.34; H, 6.36; N, 9.14; S, 3.49. Found: C, 65.41; H, 6.63; N, 9.17; S, 3.27.

(III) Production of Boc-Ser(Bzl)-Phe-D-Arg(Tos)-Tyr(Bzl)-OBzl

Using 3.90 g Boc-Phe-D-Arg(Tos)-Tyr(Bzl)-OBzl, 1.60 g Boc-Ser(Bzl)-OH, 1.08 g HONB and 1.24 g DCC, the desired product was obtained in exactly the same manner as in Example 1-(III).

Yield: 4.50 g.
m.p.: 80° to 82° C., Rf$^1$: 0.30.
[α]$_D^{25}$: +2.5°(c=1.1, in DMF).
Elemental analysis (as C$_{60}$H$_{69}$N$_7$O$_{11}$S.½H$_2$O): Calculated: C, 65.20; H, 6.38; N, 8.87; S, 2.90. Found: C, 65.29; H, 6.47; N, 9.04; S, 3.19.

(IV) Production of Boc-Asn-Ser(Bzl)-Phe-D-Arg(Tos)-Tyr(Bzl)-OBzl

Using 2.20 g Boc-Ser(Bzl)-Phe-D-Arg(Tos)-Tyr(Bzl)-OBzl, 0.61 g Boc-Asn-OH, 0.51 g HONB and 0.58 g DCC, the desired product was obtained in exactly the same manner as in Example 1-(IV).

Yield: 2.10 g (86.6%).
m.p.: 200° to 201° C., Rf$^1$: 0.30.
[α]$_D^{25}$: −17.4°(c=1.0, in DMF).
Elemental analysis (as C$_{64}$H$_{75}$N$_9$O$_{13}$S.½H$_2$O): Calculated: C, 62.93; H, 6.27; N, 10.32; S, 2.63. Found: C, 63.03; H, 6.52; N, 10.52; S, 2.91.

(V) Production of Boc-Cys(MBzl)-Asn-Ser(Bzl)-Phe-D-Arg(Tos)-Tyr(Bzl)-OBzl

The desired product was obtained with 2.0 g Boc-Asn-Ser(Bzl)-Phe-D-Arg(Tos)-Tyr(Bzl)-OBzl, 0.88 g Boc-Cys(MBzl)-OH.CHA, 0.40 g HONB and 0.46 g DCC in exactly the same manner as in Example 1-(V).

Yield: 2.20 g (92.9%).
m.p.: 90° to 92° C., Rf$^1$: 0.36.
[α]$_D^{25}$: −17.3°(c=0.9, in DMF).
Elemental analysis (as C$_{75}$H$_{88}$N$_{10}$O$_{15}$S$_2$.H$_2$O): Calculated: C, 61.96; H, 6.24; N, 9.64; S, 4.41. Found: C, 62.26; H, 6.15; N, 9.75; S, 4.55.

(VI) Production of Boc-Ala-Gln-Ser-Gly-Leu-Gly-Cys(MBzl)-Asn-Ser(Bzl)-Phe-D-Arg(Tos)-Tyr(Bzl)-OBzl Using 500 mg of the compound obtained in Example 9-(V), 241 mg Boc-Ala-Gln-Ser-Gly-Leu-Gly-OH, 126 mg HONB and 288 mg DCC, the desired product was obtained in exactly the same manner as in Example 1-(XXII).

Yield: 0.65 g (95.9%).
m.p.: 225° to 227° C. (decomposed), Rf$^2$: 0.38.
[α]$_D^{25}$: −16.2°(c=1.0, in DMF).
Elemental analysis (as C$_{96}$H$_{123}$N$_{17}$O$_{23}$S$_2$): Calculated: C, 59.21; H, 6.37; N, 12.23; S, 3.29. Found: C, 59.43; H, 6.81; N, 12.11; S, 2.99.

(VII) Production of Boc-Arg(Pme)-Met-Asp(OBzl)-Arg(Pme)-Ile-Gly-Ala-Gln-Ser-Gln-Leu-Gly-Cys(MBzl)-Asn-Ser(Bzl)-Phe-D-Arg(Tos)-Tyr(Bzl)-OBzl Using 500 mg of the compound obtained in Example 9-(VI), 384 mg Boc-Arg(Pme)-Met-Asp(OBzl)-Arg(Pme)-Ile-Gly-OH, 100 mg HONB and 360 mg DCC, the desired product was obtained in exactly the same manner as in Example 1-(XXIII).

Yield: 0.63 G (76.9%).
m.p.: 223° to 225° C. (decomposed), Rf$^2$: 0.45.
[α]$_D^{25}$: −13.8°(c=1.1, in DMF).
Elemental analysis (as C$_{154}$H$_{209}$N$_{29}$O$_{35}$S$_5$): Calculated: C, 58.04; H, 6.61; N, 12.75; S, 5.03. Found: C, 58.22; H, 6.97; N, 12.54; S, 4.92.

(VIII) Production of Boc-Cys(MBzl)-Phe-Gly-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-D-Arg(Tos)-Tyr(Bzl)-OBzl Using 300 mg of the compound obtained in Example 9-(VI), 99 mg Boc-Cys(MBzl)-Phe-Gly-Gly-OH, 50 mg HONB and 167 mg DCC, the desired product was obtained in exactly the same manner as in Example 1-(XXIV).

Yield: 270 mg (78.1%).
Elemental analysis (as C$_{178}$H$_{237}$N$_{33}$O$_{40}$S$_6$): Calculated: C, 58,23; H, 6.51; N, 12.59; S, 5.24. Found: C, 58.05; H, 6.73; N, 12.57; S, 4.87.

(IX) Production of H—Cys—Phe—Gly—Gly—Arg—Met—Asp—Arg—Ile—Gly—Ala—Gln—Ser—Gly—Leu—Gly—Cys—Asn—Ser—Phe—D—Arg—Tyr—OH([D—Arg$^{27}$]-α-hANP[7-28])

(where the Cys residues are joined by a disulfide bridge)

Using 200 mg of the compound obtained in Example 9-(VIII), the desired product was obtained via HF treatment, air oxidation and purification in exactly the same manner as in Example 1-(XXV).

Yield: 35 mg (25%).

Amino acid analysis: Asp 2.06, Ser 1.92, Glu 1.07, Gly 5.02, Ala 1.00, Half Cys 1.63, Met 0.98, Ile 1.00, Leu 1.01, Tyr 0.76, Phe 1.89, Arg 3.06.

EXAMPLE 10

Production of [D,L-Chg$^{12}$]-α-hANP[7-28]

(I) Production of
Boc-D,L-Chg-Asp(OBzl)-Arg(Pme)-Ile-Gly-OH

Using 1.0 g Boc-Asp(OBzl)-Arg(Pme)-Ile-Gly-OH.CHA, 0.30 g Boc-D,L-Chg-OH, 0.23 g HONB and 0.26 g DCC, the desired product was obtained in exactly the same manner as in Example 1-(XV).
Yield: 0.90 g (85.1%).
m.p.: 160° to 165° C., Rf$^2$: 0.44.

[α]$_D^{25}$: −15.6°(c=0.8, in DMF).
Elemental analysis (as C$_{49}$H$_{74}$N$_8$O$_{12}$S.H$_2$O): Calculated: C, 57.85; H, 7.53; N, 11.02; S, 3.15. Found: C, 57.54; H, 7.27; N, 11.17; S, 3.50.

(II) Production of
Boc-Arg(Pme)-D,L-Chg-Asp(OBzl)-Arg(Pme)-Ile-Gly-OH

Using 400 mg Boc-D,L-Chg-Asp(OBzl)-Arg(Pme)-Ile-Gly-OH, 210 mg Boc-Arg(Pme)-OH, 90 mg HONB and 100 mg DCC, the desired product was obtained in the same manner as in Example 1-(XVI).
Yield: 430 mg (78.7%).
m.p.: 146° to 147° C., Rf$^2$: 0.51.
[α]$_D^{25}$: −15.3°(c=0.9, in DMF).
Elemental analysis (as C$_{66}$H$_{100}$N$_{12}$O$_{15}$S$_2$.H$_2$O): Calculated: C, 57.29; H, 7.43; N, 12.15; S, 4.63. Found: C, 57.44; H, 7.38; N, 12.41; S, 5.16.

(III) Production of
Boc-Arg(Pme)-D,L-Chg-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXII), 225 mg Boc-Arg(Pme)-D,L-Chg-Asp(OBzl)-Arg(Pme)-Ile-Gly-OH, 60 mg HONB and 200 mg DCC, the desired product was obtained in the same manner as in Example 1-(XXIII).
Yield: 410 mg (84.1%).
m.p.: 218° to 220° C., Rf$^2$: 0.53.
[α]$_D^{25}$: −15.1°(c=1.0, in DMF).
Elemental analysis (as C$_{161}$H$_{221}$N$_{29}$O$_{35}$S$_4$): Calculated: C, 59.48; H, 6.85; N, 12.49; S, 3.94. Found: C, 59.34; H, 7.05; N, 12.55; S, 4.19.

(IV) Production of
Boc-Cys(MBzl)-Phe-Gly-Gly-Arg(Pme)-D,L,Chg-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 10-(III), 82 mg Boc-Cys(MBzl)-Phe-Gly-Gly-OH, 50 mg HONB and 167 mg DCC, the desired product was obtained in the same manner as in Example 1-(XXIV).
Yield: 295 mg (86.2%).
m.p.: 235° to 238° C.
Elemental analysis (as C$_{185}$H$_{249}$N$_{33}$O$_{40}$S$_5$): Calculated: C, 59.48; H, 6.72; N, 12.37; S, 4.29. Found: C, 59.58; H, 7.22; N, 12.22; S, 3.88.

(V) Production of H—Cys—Phe—Gly—Gly—Arg—D,L—Chg—Asp—Arg—Ile—Gly—Ala—Gln—Ser—Gly—Leu—Gly—Cys—Asn—Ser—Phe—Arg—Tyr—OH ([D,L—Chg$^{12}$]-α-hANP[7-28])

(with disulfide bond between the two Cys residues)

Using 200 mg of the compound obtained in Example 10-(IV), the desired product was obtained via HF treatment, air oxidation and purification in the same manner as in Example 1-(XXV).
Yield: 52 mg (38%).
Amino acid analysis: Asp 2.01, Ser 1.81, Glu 1.01, Gly 4.92, Ala 0.97, Half Cys 1.82, Ile 1.00, Leu 0.98, Tyr 0.84, Phe 1.90, Arg 2.99, Chg 1.15.

EXAMPLE 11

Production of [Ala$^6$]-α-hANP[6-28]

(I) Production of
Boc-Ala-Cys(MBzl)-Phe-Gly-Gly-OH

Using 300 mg Boc-Cys(MBzl)-Phe-Gly-Gly-OH, 104 mg Boc-Ala-OH, 110 mg HONB and 120 mg DCC, the desired product was obtained in the same manner as in Example 1-(XXI).
Yield: 265 mg (79.0%).
m.p.: 133° to 137° C., Rf$^2$: 0.34.
[α]$_D^{25}$: −27.0°(c=1.0, in DMF).
Elemental analysis (as C$_{32}$H$_{43}$N$_5$O$_9$S): Calculated: C, 57.04; H, 6.43; N 10.39; S, 4.76. Found: C, 57.48; H, 6.81; N, 10.16; S, 4.12.

(II) Production of
Boc-Ala-Cys(MBzl)-Phe-Gly-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXIII), 69 mg Boc-Ala-Cys(MBzl)-Phe-Gly-Gly-OH, 50 mg HONB and 167 mg DCC, the desired product was obtained in the same manner as in Example 1-(XXII).
Yield: 335 mg (95.3%).
m.p.: 2256° to 228° C. (decomposed).
Elemental analysis (as C$_{185}$H$_{250}$N$_{34}$O$_{41}$S$_6$): Calculated: C, 58.48; H, 6.65; N, 12.564; S, 5.06. Found: C, 57.96; H, 7.01; N, 12.37; S, 4.82.

(III) Production of H—Ala—Cys—Phe—Gly—Gly—Arg—Met—Asp—Arg—Ile—Gly—

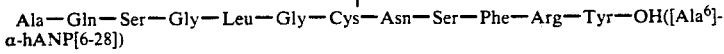
Ala—Gln—Ser—Gly—Leu—Gly—Cys—Asn—Ser—Phe—Arg—Tyr—OH([Ala⁶]-α-hANP[6-28])

Using 200 mg of the compound obtained in Example 11-(II), the desired product was obtained via HF treatment, air oxidation and purification in the same manner as in Example 1-(XXV).
Yield: 19 mg (14%).
Amino acid analysis: Asp 2.03, Ser 1.89, Glu 1.00, Gly 4.98, Ala 2.05, Half Cys 1.86, Met 1.03, Ile 1.00, Leu 1.01, Tyr 0.93, Phe 1.97, Arg 2.99.

EXAMPLE 12

Production of [D-Ala⁶]-α-hANP[6-28]

(I) Production of Boc-DAla-Cys(MBzl)-Phe-Gly-Gly-OH

Using 300 mg Boc-Cys(MBzl)-Phe-Gly-Gly-OH, 104 mg Boc-D-Ala-OH, 110 mg HONB and 120 mg DCC, the desired product was obtained in the same manner as in Example 1-(XXI).
Yield: 255 mg (76.0%).
m.p.: 153° to 156° C., Rf²: 0.29.
$[\alpha]_D^{25}$: −18.2°(c=1.0, in DMF).
Elemental analysis (as $C_{32}H_{43}N_5O_9S$): Calculated: C, 57.04; H, 6.43; N, 10.39; S, 4.76. Found: C ,57.24; H, 6.55; N, 9.98; S, 4.32.

(II) Production of Boc-D-Ala-Cys(MBzl)-Phe-Gly-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXIII), 69 mg Boc-D-Ala-Cys(MBzl)-Phe-Gly-Gly-OH, 50 mg HONB and 167 mg DCC, the desired product was obtained in the same manner as in Example 1-(XXIII).
Yield: 325 mg (92.5%).
m.p.: 222° to 227° C. (decomposed).
Elemental analysis (as $C_{185}H_{250}N_{34}O_{41}S_6$): Calculated: C, 58.48; H, 6.65; N, 12.54; S, 5.06. Found: C, 58.07; H, 6.84; N, 12.39; S, 4.85.

OH, 230 mg HONB and 262 mg DCC), the desired product was obtained in the same manner as in Example 1-(XV).
Yield: 0.93 g (87.8%).
m.p.: 148°–153° C., Rf²: 0.47.
$[\alpha]_D^{25}$: −14.9°(c=1.0, in DMF).
Elemental analysis (as $C_{47}H_{72}N_8O_{12}S$) Calculated: C, 58.01; H, 7.46; N, 11.51; S, 3.29. Found: C, 57.77; H, 7.76; N 11.34; S, 3.21.

(II) Production of Boc-Arg(Pme)-Leu-Asp(OBzl)-Arg(Pme)-Ile-Gly-OHl

Using 0.39 g Boc-Leu-Asp(OBzl)-Arg(Pme)-Ile-Gly-OH, Boc-Arg(Pme)-ONB (prepared with 0.21 g Boc-Arg(Pme)-OH, 90 mg HONB and 100 mg DCC), the desired product was obtained in the same manner as in Example 1-(XVI).
Yield: 403 mg (73.2%).
m.p.: 154°–158° C., Rf²: 0.46.
$[\alpha]_D^{25}$: −12.6°(c=1.0, in DMF).
Elemental analysis (as $C_{64}H_{97}N_{12}O_{15}S_2$): Calculated: C, 57.42; H, 7.30; N, 12.56; S ,4.79. Found: C, 57.44; H, 7.63; N, 11.98; S, 4.82.

(III) Production of Boc-Arg(Pme)-Leu-Asp(OBzl)-Arg(Pme)-Ile-Gly-Ala-Gln-Ser-Gly-Leu-Gly-Cys(MBzl-Asn-Ser(Bzl)-Phe-Arg(Pme)-Tyr(Bzl)-OBzl Using 300 mg of the compound obtained in Example 1-(XXII), 221 mg Boc-Arg(Pme)-Leu-Asp(OBzl)-Arg(Pme)-Ile-Gly-OH, 60 mg HONB and 200 mg DCC), the desired product was obtained in the same manner as in Example 1-(XXII).
Yield: 0.48 g (quantitative)
m.p.: 205°14 208° C. (decomposed), Rf²: 0.43.
$[\alpha]_D^{25}$: −11.7°(c=1.0, in DMF).
Elemental analysis (as $C_{159}H_{219}N_{29}O_{35}S_4$): Calculated: C, 59.22; H, 6.84; N, 12.61; S, 3.98. Found: C 60.36; H, 6.94; N, 12.33; S, 3.71.

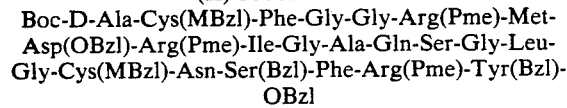
(III) Production of H—D—Ala—Cys—Phe—Gly—Gly—Arg—Met—Asp—Arg—Ile—Gly—
Ala—Gln—Ser—Gly—Leu—Gly—Cys—Asn—Ser—Phe—Arg—Tyr—OH([D—Ala⁶]-α-hANP[6-28])

Using 200 mg of the compound obtained in Example 12, the desired product was obtained via HF treatment, air oxidation and purification in the same manner as in Example 1-(XXV).
Yield: 23 mg (17%).
Amino acid analysis: Asp 2.04, Ser 1.88, Glu 0.98, Gly 4.01, Ala 2.00, Half Cys 1.90, Met 0.97, Ile 1.00, Leu 1.03, Tyr 0.94, Phe 2.03, Arg 3.02.

EXAMPLE 13

Production of [Aib⁶, Leu¹²]α-hANP[6-28]

(I) Production of Boc-Leu-asp(OBzl)-Arg(Pme)-Ile-Gly-OH

Using 1.0 g Boc-Asp(OBzl)-Arg(Pme)-Ile-Gly-OH.CHA and HONB (prepared with 279 mg Boc-Leu- (IV) Production of Boc-Aib-Cys(MBzl)-Phe-Gly-Gly-Arg(Pme)-Leu-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 13-(III), 74 mg Boc-Aib-Cys(MBzl)-Phe-Gly-Gly-OH, 50 mg HONB and 200 mg DCC, the desired product was obtained in the same manner as in Example 1-(XXII).
Yield: 298 mg (84.4%).
m.p.: 220°–225° C., (decomposed).

Elemental analysis (as $C_{183}H_{254}N_{34}O_{39}S_5$): Calculated: C, 59.17; H, 6.89; N, 12.82; S, 4.32. Found: C, 59.50; H, 7.08; N, 12.50; S, 4.11.

$[\alpha]_D^{25}$: $-11.0°$ (c=1.0, in DMF).
Elemental analysis (as $C_{159}H_{219}N_{29}O_{35}S_4$) Calculated: C, 59.22; H, 6.84; N, 12.61; S, 3.98. Found: C, 59.69; H, 6.95; N, 12.42; S, 3.94.

(V) Production of H—Aib—Cys—Phe—Gly—Gly—Arg—Leu—Asp—Arg—Ile—Gly—Ala—Gln—Ser—Gly—Leu—Gly—Cys—Asn—Ser—Phe—Arg—Tyr—OH([Aib$^6$, Leu$^{12}$]-α-hANP[6-28])

Using 200 mg of the compound obtained in Example 13-(IV), the desired product was obtained via HF treatment, air oxidation and purification in the same manner as in Example 1-(XXV).
Yield: 30 mg (22%).
Amino acid analysis: Asp 1.96, Ser 1.85, Glu 1.04, Gly 4.98, Ala 1.00, Half Cys 1.87, Ile 1.00, Leu 1.98, Tyr 0.89, Phe 2.04, Arg 3.05, Aib 0.94.

EXAMPLE 14

Production of [Aib$^6$, Nle$^{12}$]-α-hANP[6-28]

(I) Using 1.0 g Boc-Asp(OBzl)-Arg(Pme)-Ile-Gly-OH.CHA and Boc-Nle ONB (prepared with 279 g Boc-Nle-OH, 230 mg HONB and 262 mg DCC), the desired product was obtained in the same manner as in Example 1-(XV).

Yield: 1.03 g (97.0%).
m.p.: 162°-167° C. Rf$^2$: 0.43.
$[\alpha]_D^{25}$: $-13.5°$ (c=1.0, in DMF).
Elemental analysis (as $C_{47}H_{72}N_8O_{12}S$): Calculated: C, 58.01; H, 7.46; N, 11.51; S, 3.29. Found: C, 57.85; H, 7.60; N, 11.36; S, 3.09.

(II) Production of Boc-Arg(Pme)-Nle-Asp(OBzl)-Arg(Pme)-Ile-Gly-OH

Using 0.39 g Boc-Nle-Asp(OBzl)-Arg(Pme)-Ile-Gly-OH and Boc-Arg(Pme)-OND (prepared with 0.21 g Boc-Arg(Pme)-OH, 90 mg HONB and 100 mg DCC), the desired product was obtained in the same manner as in Example 1-(XVI).
Yield: 403 mg (73.2%).
m.p.: 171°-177° C., Rf$^2$: 0.49.
$[\alpha]_D^{25}$: $-10.6°$ (c=1.0, in DMF).
Elemental analysis (as $C_{64}H_{97}N_{12}O_{15}S_2$) Calculated: C, 57.42; H, 7.30; N, 12.56; S, 4.79. Found: C, 57.51; H, 7.57; N, 12.32; S, 4.97.

(III) Production of Boc-Arg(Pme)-Nle-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXII), 221 mg Boc-Arg(Pme)-Nle-Asp(OBzl)-Arg(Pme)-Ile-Gly-OH. 60 mg HONB and 200 mg DCC, the desired product was obtained in the same manner as in Example 1-(XXII).
Yield: 0.48 g (quantitative).
m.p.: 205°-208° C. Rf$^2$: 0.41.

(IV) Production of Boc-Aib-Cys(MBzl)-Phe-Gly-Gly-Arg(Pme)-Nle-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 14-(III), 74 mg Boc-Aib-Cys(MBzl)-Phe-Gly-Gly-OH, 50 mg HONB and 200 mg DCC, the desired product was obtained in the same manner as in Example 1-(XXII).
Yield: 280 mg (82.5%).
m.p.: 225°14 228° C., (decomposed).
Elementaly analysis (as $C_{183}H_{254}N_{34}O_{39}S_5$). Calculated: C, 59.17; H, 6.89; N, 12.82; S, 4.32. Found: C, 59.30; H, 7.03; N, 12.44; S, 4.16.

(V) Production of H—Aib—Cys—Phe—Gly—Gly—Arg—Nle—Asp—Arg—Ile—Gly—Ala—Gln—Ser—Gly—Leu—Gly—Cys—Asn—Ser—Phe—Arg—Tyr—OH([Aib$^6$, Nle$^{12}$]-α-hANP[6-28])

Using 200 mg of the compound obtained in Example 14-(IV), the desired product was obtained via HF treatment, air oxidation and purification in the same manner as in Example 1-(XXV).
Yield: 20 mg (14.4%).
Amino acid analysis: Asp 2.02, Ser 1.89, Glu 0.98, Gly 4.97, Ala 1.01, Half Cys 1.88, Ile 1.00, Leu 1.02, Tyr 0.94, Phe 2.02, Arg 3.03, Aib 0.96, Nle 0.97.

EXAMPLE 15

Production of [Val$^6$]-αhANP[6-28]

(I) Production of Boc-Val-Cys(MBzl)-Phe-Gly-Gly-OH

Using 300 mg Boc-Cys(MBzl)-Phe-Gly-Gly-OH, 118 mg Boc-Val-OH, 110 mg HONB and 124 mg DCC, the desired product was obtained in the same manner as in Example 1-(XXI).
Yield: 324 mg (92.7%).
m.p.: 146°-150° C. Rf$^2$: 0.42.
$[\alpha]_D^{25}$: $-20.7°$ (c=1.0, in DMF).
Elemental analysis (as $C_{34}H_{47}N_5O_9S$). Calculated: C, 58.19; H, 6.75; N, 9.98; S, 4.57. Found: C, 58.43; H, 6.94; N, 10.08; S, 4.26.

(II) Production of Boc-Val-Cys(MBzl)-Phe-Gly-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXIII), 72 mg Boc-Val-Cys(MBzl)-Phe-Gly-Gly- OH, HONB 50 mg and 176 mg DCC, the desired product was obtained in the same manner as in Example 1-(XXII).

Yield: 323 mg (9.2%).
m.p.: 222°–230° C. (decomposed).
Elemental analysis (as $C_{187}H_{254}N_{34}O_{41}S_5$). Calculated: C, 59.19; H, 6.75; N, 12.55; S, 4.23. Found: C, 59.05; H, 6.97; N, 12.29; S, 4.25.

(II) Production of Boc-Ile-Cys(MBzl)-Phe-Gly-Gly-Arg(Pme)-Met-Asp(OBzl)-Arg(Pme)-Ile-Gly-Ala-Gln-Ser-Gly-Leu-Gly-Cys(MBzl)-Asn-Ser(Bzl)-Phe-Arg(Pme)-Tyr(Bzl)-OBzl Using 300 mg of the compound obtained in Example 1-(XXIII), 73 mg Boc-Ile-Cys(MBzl)-Phe-Gly-Gly- (III) Production of H—Val—Cys—Phe—Gly—Gly—Arg—Met—Asp—Arg—Ile—Gly—Ala—Gln—Ser—Gly—Leu—Gly—Cys—Asn—Ser—Phe—Arg—Tyr—OH([Val⁶]-αhANP[6-28])

Using 200 mg of the compound obtained in Example 15-(II), the desired product was obtained via HF treatment, air oxidation and purification in the same manner as in Example 1-(XXV).

Yield: 21 mg (16%).
Amino acid analysis: Asp 1.98, Ser 1.86, Glu 0.98, Gly 5.06, Ala 1.01, Half Cys 1.86, Met 1.02, Ile 1.00, Leu 0.99, Tyr 0.91, Phe 2.04, Arg 2.99, Val 0.97.

OH, 50 mg HONB and 167 mg DCC, the desired product was obtained in the same manner as in Example 1-(XXII).

Yield: 338 mg (95.2%).
m.p.: 216°–226° C. (decomposed).
Elemental analysis (as $C_{188}H_{256}N_{34}O_{41}S_5$). Calculated: C, 59.29; H, 6.77; N, 12.50; S, 4.21. Found: C, 59.16; H, 6.98; N, 12.21; S, 4.16.

(III) Production of H—Ile—Cys—Phe—Gly—Gly—Arg—Met—Asp—Arg—Ile—Gly—Ala—Gln—Ser—Gly—Leu—Gly—Cys—Asn—Ser—Phe—Arg—Tyr—OH([Ile⁶]-αhANP[6-28])

Using 200 mg of the compound obtained in Example 16-(II), the desired product was obtained via HF treatment, air oxidation and purification in the same manner as in Example (XXV).

Yield: 15 mg (11%).
Amino acid analysis: Asp 2.01, Ser 1.90, Glu 0.97, Gly 4.98, Ala 1.02, Half Cys 1.89, Met 0.97, Ile 2.00, Leu 1.01, Tyr 0.94, Phe 1.98, Arg 3.03

What is claimed is:

1. A peptide derivative of the formula

A-Cys-Phe-Gly-Arg-Met-Asp-Arg-Ile-Gly-Ala-Gln-Ser-Gly-Leu-Gly-Cys-Asn-Ser-Phe-D-Arg-Tyr-OH

EXAMPLE 16

Production of [Ile⁶]-αhANP[6-28]

(I) Production of Boc-Ile-Cys(MBzl)-Phe-Gly-Gly-OH

Using 300 mg Boc-Cys(MBzl)-Phe-Gly-Gly-OH, 131 mg Boc-Ile-OH·½H₂O, 110 mg HONB and 120 mg DCC, the desired product was obtained in the same manner as in Example 1-(XXII).

Yield: 296 mg (83.0%).
m.p.: 146°–150° C. Rf²: 0.45.
Elemental analysis (as $C_{35}H_{49}N_5O_9S$).
$[\alpha]_D^{25}$: −22.3°(c=1.0, in DMF). Calculated: C, 58.72; H, 6.90; N, 9.78; S, 4.48. Found: C, 58.53; H, 6.94; N, 9.65; S, 4.55.

wherein A is alpha-amino isobutyric acid, Ala or D-Ala, or its pharmaceutically acceptable salt.

2. The peptide derivative according to claim 1, wherein A is alpha-amino isobutyric acid.

3. The peptide derivative according to claim 1, wherein A is Ala.

4. The peptide derivative according to claim 1, wherein A is D-Ala.

* * * * *